US007544775B2

(12) United States Patent
Falson et al.

(10) Patent No.: US 7,544,775 B2
(45) Date of Patent: Jun. 9, 2009

(54) SYSTEMS FOR EXPRESSING TOXIC PROTEINS, VECTORS AND METHOD OF PRODUCING TOXIC PROTEINS

(75) Inventors: Pierre Falson, Sainte Foy les Lyon (FR); François Penin, Decines (FR); Cédric Montigny, Gif sur Yvette (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 109 days.

(21) Appl. No.: 10/528,344

(22) PCT Filed: Sep. 19, 2003

(86) PCT No.: PCT/FR03/02763

§ 371 (c)(1),
(2), (4) Date: Nov. 8, 2005

(87) PCT Pub. No.: WO2004/027068

PCT Pub. Date: Apr. 1, 2004

(65) Prior Publication Data

US 2006/0173165 A1    Aug. 3, 2006

(30) Foreign Application Priority Data

Sep. 20, 2002    (FR)    ................... 02 11676

(51) Int. Cl.
*C07K 14/00* (2006.01)
*C12N 15/11* (2006.01)
*C12N 7/00* (2006.01)

(52) U.S. Cl. .................... 530/350; 536/23.1; 424/218.1

(58) Field of Classification Search ........................ None
See application file for complete search history.

(56) References Cited

U.S. PATENT DOCUMENTS 5,322,769 A * 6/1994 Bolling et al. .................. 435/5
6,881,558 B1 * 4/2005 Weiner et al. .............. 435/91.1

FOREIGN PATENT DOCUMENTS

EP    0 212 532    *    3/1987

OTHER PUBLICATIONS

Wang et al. Journal of Biotechnology, 2002, vol. 94, p. 235-244.*
De Beeck et al. Journal of Biological Chemistry, 2000, vol. 275, p. 31428-31437, in IDS of Jun. 23, 2005.*
Caccaglione et al. Virus Genes, 2000, vol. 21, p. 223-226, in IDS of Jun. 23, 2005.*
Arechaga et al. FEBS, 2000, vol. 482, p. 215-219.*
Smith et al. Gene, 1988, vol. 67, p. 31-40.*
Fiaschi et al. FEBS, 1995, vol. 367, p. 145-148.*
Search Report from French Application 0211676 dated Jun. 12, 2003.
Wang, Y, et al., "A unique approach for high level expression and production of a recombinant cobra neurotoxin in *Escherichia coli*", *Journal of Biotechnology* vol. 94 No. 3:235-244 (2002).

Ciccaglione, A.R., et al., "Hepatitis C Virus E1 Protein Induces Modification of Membrane Permeability in *E. coli* Cells", *Virology* 250:1-8 (1998).
Ciccaglione, A.R., et al., "Secretion and purification of HCV E1 protein forms as glutathione-*S*-transferase fusion in the baculovirus insect cell system", *Virus Research* 55:157-165 (1998).
Okamoto, H., et al., "The 5'-terminal sequence of the hepatitis C virus genome", abstract from EMBL GenBank DDBJ databases, Feb. 1992.
Sarrazin, C., et al., "Quasispecies heterogeneity of the carboxyterminal part of the E2 gene including the PePHD and sensitivity of hepatitis C virus 1b isolates to antiviral therapy", abstract from EMBL GenBank DDBJ databases, Jul. 2001.
Christendat, D., et al., "Structural proteomics: prospects for high throughput sample preparation", *Progress in Biophysics & Molecular Biology* 73:339-345 (2000).
Hammarström, M., et al., "Rapid screening for improved solubility of small human proteins produces as fusion proteins in *Escherichia coli*", *Protein Science* 11:313-321 (2002).
Elble, R., "An Efficient Procedure to Dialyze Volumes in the Range of 10-200 µl", *Biotechniques* 13(1) (1992).
Falson, P. "Improved Phenol-Based Method for the Isolation of DNA Fragments from Low Melting Temperature-Argarose Gels", Biotechniques 13(1):20-22 (1992).
Falson, P, et al., "Functional Nucleotide-Binding Domain in the $F_0$-$F_1$-ATPsynthase α Submit from the Yeast *Schizosaccharomyces pombe*", *Biochemistry* 32:10387-10397 (1993).
Ciccaglione, A.R., et al., "Expression and Membrane Association of Hepatitis C Virus Envelope 1 Protein", *Virus Genes* 21(3):223-226 (2000).
Sisk, W.P., et al., "Deletion of hydrophobic domains of viral glycoproteins increases the level of their production in *Escherichia coli*", *Gene* 112:157-162 (1992).
Paulsen, I.T., et al., "Unified inventory of established and putative transporters encoded within the complete genome of *Saccharomyces cerevisiae*", *FEBS Letters*, 430:116-125 (1998).
Decottignies A., et al., "Complete inventory of the yeast ABC proteins", *nature genetics* 15:137-145 (1997).

(Continued)

*Primary Examiner*—Larry R. Helms
*Assistant Examiner*—Agnieszka Boesen
(74) *Attorney, Agent, or Firm*—Buchanan Ingersoll & Rooney PC

(57) ABSTRACT

The present invention relates to a system for expressing toxic proteins, to an expression vector comprising this system, to a prokaryotic cell transformed with this system, and also to a method for synthesizing a toxic protein using this expression system. The expression system of the invention is characterized in that it comprises successively, in the 5'-3' direction, a nucleotide sequence encoding the Asp-Pro dipeptide and a nucleotide sequence encoding a toxic protein. According to a preferred embodiment of the invention, the expression system also comprises, upstream of the Asp-Pro sequence, a nucleotide sequence encoding a soluble protein. The expression system of the invention makes it possible to construct an expression vector that is useful for transforming a prokaryotic cell such as *E. coli*, for example in a method for synthesizing the toxic protein.

13 Claims, 9 Drawing Sheets

OTHER PUBLICATIONS

Arechaga, I., "Characterization of new intracellular membranes in *Escherichia coli* accompanying large scale over-production of the b subunit of $F_1F_0$ ATP synthase", *FEBS Letters* 482:215-219 (2000).

Miroux, B. and Walker, J.E., "Over-production of Proteins in *Escherichia coli*: Mutant Hosts that Allow Synthesis of some Membrane Proteins and Globular Proteins at High Levels", *J. Mol. Biol.* 260:289-298 (1996).

Mayo, M.A. and Pringle, C.R., "Virus Taxonomy", *Journal of General Virology* 79:649-657 (1998).

De Beeck, A.O., et al., "The Transmembrane Domains of Hepatitis C Virus Envelope Glycoproteins E1 and E2 Play a Major Role in Heterodimerization", *The Journal of Chemistry* 275(40):31428-31437 (2000).

Choo, Q.L., et al., "Isolation of a cDNA Clone Derived from a Blood-Borne Non-A, Non-B Viral Hepatitis Genome", *Science* 244:359-362 (1989).

De Beeck, A.O., et al., "Biogenesis of hepatitis C virus envelope glycoproteins", *Journal of General Virology* 82:2589-2595 (2001).

Sharp, P.M., et al., "Codon usage patterns *Escherichia coli, Bacillus subtilis, Saccharomyces cerevisiae, Schizosaccharomyces pombe, Drosophia melanogaster* and *Homo sapiens*; a review of the considerable within-species diversity" *Nucleic Acids Research* 16(17):8207-8211 (1988).

Mullis, K.B. and Faloona, F.A., "Specific Synthesis of DNA in Vitro via a Polymerase-Catalyzed Chain Reaction", *Methods in Enzymology* 155:335-350 (1987).

Tabor, S. and Richardson, C.C., "A bacteriophase T7 RNA polymerase/promoter system for controlled exclusive expression of specific genes", *Proc. Natl. Acad. Sci., USA* 82:1074-1078 (1985).

Guan, K.L., and Dixon, J.E., "Eukaryotic Proteins Expressed in *Escherichia coli*: An Improved Thrombin Cleavage and Purification Procedure of Fusion Proteins with Glutathione *S*-Transferase", *Analytical Biochemistry* 192:262-267 (1991).

Hakes, D.J. and Dixon, J.E., "New Vectors for High Level Expression of Recombinant Proteins in Bacteria", *Analytical Biochemistry* 202:293-298 (1992).

Tabor, S., "Expression Using the T7 RNA Polymerase/Promoter System", *Current Protocols* Supplement 11, Unit 16.2 (1990).

Schägger, H. and von Jagow, G., "Tricine-Sodium Dodecyl Sulfate-Polyacrylamide Gel Electrophoresis for the Separation of Proteins in the Range from 1 to 100 kDa", *Analytical Biochemistry* 166:368-379 (1987).

Laemmli, U.K., "Cleavage of Structural Proteins during the Assembly of the Head of Bacteriophase T4", *Nature* 227:680-685 (1970).

Sambrook, et al., "Expression of Cloned Genes in *Escherichia coli*", Chapter 17, A laboratory manual, second edition, Cold Spring Harbor Laboratory Press (1989).

"Detection and Analysis of Proteins Expressed from Cloned Genes", Chapter 18, A laboratory manual, second edition, Cold Spring Harbor Laboratory Press (1989).

\* cited by examiner

A $_{367}$MIAGAHWGVLAGIAYFSMVGNMAKVLVLIVVLLLEFAGVDA$_{303}$, 37,aa, 3861 Da.

B

```
N°      1  2  3  4  5  6  7  8  9 10 11 12 13 14 15 16 17 18 19 ..
aa      M  I  A  G  A  H  W  G  V  L  A  G  I  A  Y  F  S  M  V ..
Seq  ATGATCGCTGGTGCTCACTGGGGTGTTCTGGCTGTATCGCTTACTTCTCTATGGTT..
        1        10        20        30        40        50

N°   ..20 21 22 23 24 25 26 27 28 29 30 31 32 33 34 35 36 37
aa   ..G  N  W  A  K  V  L  V  V  L  L  L  F  A  G  V  D  A
Seq  ..GGTAACTGGGCTAAAGTTCTGGTTGTTCTGCTGCTGTTCGCTGGTGTTGACGCT
       60        70        80        90       100       111
```

C

```
           NdeI
5'_GGGAATGCCATATGATCGCTGGTG_3'
   5'_ATGCCATATGATCGCTGGTGCTCACTGGGGTGTTCTGGCTGTATCGCTTACTTCTCTATGGTTGGTAAC..
   3'_TACGGTATACTAGCGACCACGAGTGACCCCACAGACCGACATAGCGAATGAAGAGATACCAACCATTG..

ClaI
..TGGGCTAAAGTTCTGGTTGTTCTGCTGCTGTTCGCTGGTGTTGACGCTTAGATCGATATGC_3'   131 bases
..ACCCGATTTCAAGACCAACAAGACGACGACAAGCGACCACAAGCTGGAATCTAGCTATACG_5'
                                        3'_ACAACTGGAATCTAGCTATACG_5'
```

OL11(+): 5'atgccatatgatcgctggtgtctcactgggtgttctgctgtatcgcttacttctctatgttggtaactggg
OL12(-): 5'gcatatcgatcctaagcgtcaacaccagcgaacagcagcagaacaaccagaacttagcccagttaccaaccatagagaa Cloning in pT7-7:
OL13(+): 5'gggaatgccatatgatcgctggtg
OL14(-): 5'gcatatcgatcctaagcgtcaaca Cloning in pGEXKT:
OL15(+): 5'ggatccatgaatacgttgttc (without DP site)
OL17(+): 5'ggatccgacccgatgaatacgttgttc (with DP site)
OL16(-): 5'gaattcctaagcttcagcctgag Cloning in pET32a:
OL18(+): 5'gtgatatctgatctgtctggtggtggt (hybridizes to the segment 915-932 of pGEXKT)
OL16(-): 5'gaattcctaagcttcagcctgag Cloning in pT7-7 of (M)DP-TME1::
OL19 (+) : 5'- CGCA<u>TATG</u>GACCCGATGCGCTGGTGCT -3' (Nde I underlined)
OL20 (-) : 5'-<u>GAATTCC</u>TAAGCGTCAACACCAGC-3' (EcoR I underlined)

FIG. 2

A  (M)₇₁₇EYVVLLFLLLADARVCSCLWMMLISQAEA₇₄₆                31 aa, 3546 Da.

B
N°       1  2  3  4  5  6  7  8  9 10 11 12 13 14 15 16 ..
Aa       M  E  Y  V  V  L  L  F  L  L  L  A  D  A  R  V ..
Seq  ATGGAATACGTTGTTCTGCTGTTCCTGCTGCTGGCTGACGCTCGTGTT..
     1           10           20           30          40

N°      17 18 19 20 21 22 23 24 25 26 27 28 29 30 31
Aa   .. C  S  C  L  W  M  M  L  L  I  S  Q  A  E  A
Seq ..TGCTCTTGCCTGTGGATGATGCTGCTGATCTCTCAGGCTGAAGCT
             50           60           70           80        90 93

C
       NdeI
5'-CATATGGAATACGTTGTTC_3'
(+) 5'-CATATGGAATACGTTGTTCTGCTGTTCCTGCTGCTGGCTGACGCTCGTGTT..
(-) 3'-GTATACCTTATGCAACAAGACGACAAGGACGACGACCGACTGCGAGCACAA..

Hind III
..TGCTCTTGCCTGTGGATGATGCTGCTGATCTCTCAGGCTGAAGCTTAAGCTT-3'   117 bp
..ACGAGAACGGACACCTACGACGACGACTAGAGAGTCCGACTTCGAATTCGAA-5'
                                        3'-GACTAGAGAGTCCGACTTCGAATTCGAA-5'

OL21(+): 5'catatggaatacgttgttctgctgttcctgctggctgacgctcgtgtttgctcctgtggat
OL22(-): 5'aagcttaagcttcagcctgagagatcagcagcatcatccacaggcaagagcaaacac Cloning in pT7-7:
OL23(+): 5'catatggaatacgttgttc
OL24(-): 5'aagcttaagcttcagcctgagagatcag Cloning in pGEXKT:
OL25(+): 5'ggatccgaatacgttgttc (without DP site)
OL27(+): 5'ggatccgacccggaatacgttgttc (with DP site)
OL26(-): 5'gaattcttaagcttcagcctgagagatcag Cloning in pET32a:
OL18(+): 5'gtgatatctgatctgtctggtggt (hybridizes to the segment 915-932 of pGEXKT)
OL26(-): 5'gaattcttaagcttcagcctgagagatcag Cloning in pT7-7 of (M)DP-TME2:
OL28 (+) : 5'- CGCATATGGACCCGGAATACGTTGTTC-3' (Nde I underlined)
OL29 (-) : 5'-CAGAATTCCTAAGCTTCAGCCTGAGAG-3' (EcoR I underlined)

FIG. 3

GST :
MSPILGYWKIKGLVQPTRLLLEYLEEKYEEHLYERDEGDKWRNKKFELGLEFPNLPYYIDGDVKLTQSMAIIRYI
ADKHNMLGGCPKERAEISMLEGAVLDIRYGVSRIAYSKDFETLKVDELSKLPEMLKMFEDRLCHKTYLNGDHVTH
PDFMLYDALDVVLYMDPMCLDAFPKLVCFKKRIEAIPQIDKYLKSSKYIAWPLQGWQATFGGGDHPPKSDLSGGG
GGLVPRGS/PGIHRD

GST-TME2 :
MSPILGYWKIKGLVQPTRLLLEYLEEKYEEHLYERDEGDKWRNKKFELGLEFPNLPYYIDGDVKLTQSMAIIRYIA
DKHNMLGGCPKERAEISMLEGAVLDIRYGVSRIAYSKDFETLKVDELSKLPEMLKMFEDRLCHKTYLNGDHVTHPD
FMLYDALDVVLYMDPMCLDAFPKLVCFKKRIEAIPQIDKYLKSSKYIAWPLQGWQATFGGGDHPPKSDLSGGGGGL
VPRGS/EYVLLFLLLADARVCSCLWMLLISQAEA

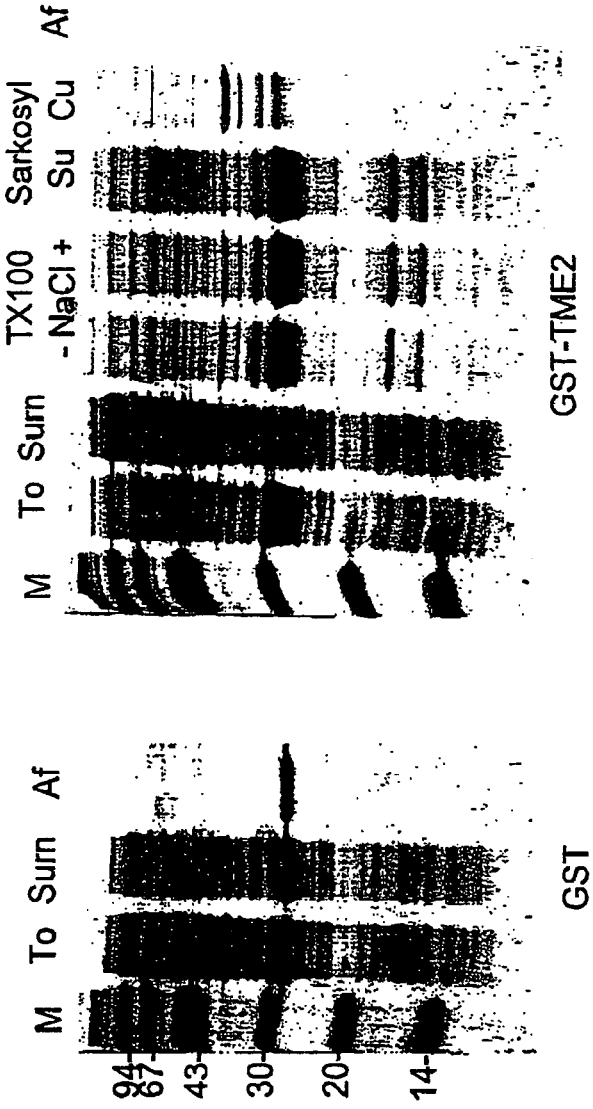

FIG. 6

SEQUENCE LISTING

```
<160> NUMBER OF SEQ ID NOS: 53

<210> SEQ ID NO 1
<211> LENGTH: 37
<212> TYPE: PRT
<213> ORGANISM: Hepatitis C virus

<400> SEQUENCE: 1

Met Ile Ala Gly Ala His Trp Gly Val Leu Ala Gly Ile Ala Tyr Phe
  1               5                  10                  15

Ser Met Val Gly Asn Trp Ala Lys Val Leu Val Val Leu Leu Leu Phe
             20                  25                  30

Ala Gly Val Asp Ala
         35

<210> SEQ ID NO 2
<211> LENGTH: 31
<212> TYPE: PRT
<213> ORGANISM: Hepatitis C virus

<400> SEQUENCE: 2

Met Glu Tyr Val Val Leu Leu Phe Leu Leu Leu Ala Asp Ala Arg Val
  1               5                  10                  15

Cys Ser Cys Leu Trp Met Met Leu Leu Ile Ser Gln Ala Glu Ala
             20                  25                  30

<210> SEQ ID NO 3
<211> LENGTH: 111
<212> TYPE: DNA
<213> ORGANISM: Hepatitis C virus

<400> SEQUENCE: 3
atgatcgctg gtgctcactg gggtgttctg gctggtatcg cttacttctc tatggttggt      60
aactgggcta aagttctggt tgttctgctg ctgttcgctg gtgttgacgc t              111

<210> SEQ ID NO 4
<211> LENGTH: 93
<212> TYPE: DNA
<213> ORGANISM: Hepatitis C virus

<400> SEQUENCE: 4
atggaatacg ttgttctgct gttcctgctg ctggctgacg ctcgtgtttg ctcttgcctg      60
tggatgatgc tgctgatctc tcaggctgaa gct                                  93

<210> SEQ ID NO 5
<211> LENGTH: 24
<212> TYPE: DNA
<213> ORGANISM: Artificial sequence
<220> FEATURE:
<223> OTHER INFORMATION: Description of the artificial sequence:
      oligonucleotide (+) of insertion into pT7-7
```

<400> SEQUENCE: 5
gggaatgcca tatgatcgct ggtg                                              24

<210> SEQ ID NO 6
<211> LENGTH: 23
<212> TYPE: DNA
<213> ORGANISM: Artificial sequence
<220> FEATURE:
<223> OTHER INFORMATION: Description of the artificial sequence:
      oligonucleotide (-) of insertion into pT7-7

<400> SEQUENCE: 6
gcatatcgat ctaagcgtca aca                                               23

<210> SEQ ID NO 7
<211> LENGTH: 131
<212> TYPE: DNA
<213> ORGANISM: Artificial sequence
<220> FEATURE:
<223> OTHER INFORMATION: Description of the artificial sequence: TME1
      coding sens DNA + 3' cla I site

<400> SEQUENCE: 7
atgccatatg atcgctggtg ctcactgggg tgttctggct ggtatcgctt acttctctat       60
ggttggtaac tgggctaaag ttctggttgt tctgctgctg ttcgctggtg ttgacgctta      120
gatcgatatg c                                                           131

<210> SEQ ID NO 8
<211> LENGTH: 131
<212> TYPE: DNA
<213> ORGANISM: Artificial sequence
<220> FEATURE:
<223> OTHER INFORMATION: Description of the artificial sequence:
      anticodant sens DNA + 5' cla I site

<400> SEQUENCE: 8
gcatatcgat ctaagcgtca acaccagcga acagcagcag aacaaccaga actttagccc       60
agttaccaac catagagaag taagcgatac cagccagaac accccagtga gcaccagcga      120
tcatatggca t                                                           131

<210> SEQ ID NO 9
<211> LENGTH: 74
<212> TYPE: DNA
<213> ORGANISM: Artificial sequence
<220> FEATURE:
<223> OTHER INFORMATION: Description of the artificial sequence:
      coding sens oligonucleotide for the synthesis of
      TME1

<400> SEQUENCE: 9
atgccatatg atcgctggtg ctcactgggg tgttctggct ggtatcgctt acttctctat       60
ggttggtaac tggg                                                         74

<210> SEQ ID NO 10
<211> LENGTH: 79
<212> TYPE: DNA
<213> ORGANISM: Artificial sequence
<220> FEATURE:
<223> OTHER INFORMATION: Description of the artificial sequence:
      anticoding sens oligonucleotide for the synthesis of
      TME1

<400> SEQUENCE: 10

```
gcatatcgat ctaagcgtca acaccagcga acagcagcag aacaaccaga actttagccc    60
agttaccaac catagagaa                                                 79
```

```
<210> SEQ ID NO 11
<211> LENGTH: 22
<212> TYPE: DNA
<213> ORGANISM: Artificial sequence
<220> FEATURE:
<223> OTHER INFORMATION: Description of the artificial sequence:
      oligonucleotide (+) of insertion into pGEXKT without
      the dp site

<400> SEQUENCE: 11
ggatccatgg aatacgttgt tc                                             22

<210> SEQ ID NO 12
<211> LENGTH: 28
<212> TYPE: DNA
<213> ORGANISM: Artificial sequence
<220> FEATURE:
<223> OTHER INFORMATION: Description of the artificial sequence:
      oligonucleotide (+) of insertion into pGEXKT with
      the dp site

<400> SEQUENCE: 12
ggatccgacc cgatggaata cgttgttc                                       28

<210> SEQ ID NO 13
<211> LENGTH: 23
<212> TYPE: DNA
<213> ORGANISM: Artificial sequence
<220> FEATURE:
<223> OTHER INFORMATION: Description of the artificial sequence:
      oligonucleotide (-) of insertion into pGEXKT

<400> SEQUENCE: 13
gaattcctaa gcttcagcct gag                                            23

<210> SEQ ID NO 14
<211> LENGTH: 27
<212> TYPE: DNA
<213> ORGANISM: Artificial sequence
<220> FEATURE:
<223> OTHER INFORMATION: Description of the artificial sequence:
      oligonucleotide (+) of transfert onto pET32a

<400> SEQUENCE: 14
gtgatatctg atctgtctgg tggtggt                                        27

<210> SEQ ID NO 15
<211> LENGTH: 26
<212> TYPE: DNA
<213> ORGANISM: Artificial sequence
<220> FEATURE:
<223> OTHER INFORMATION: Description of the artificial sequence:
      oligonucleotide (+) of insertion into pT7-7

<400> SEQUENCE: 15
cgcatatgga cccgatcgct ggtgct                                         26

<210> SEQ ID NO 16
<211> LENGTH: 24
<212> TYPE: DNA
<213> ORGANISM: Artificial sequence
<220> FEATURE:
<223> OTHER INFORMATION: Description of the artificial sequence:
``` oligonucleotide (-) of insertion into pT7-7

<400> SEQUENCE: 16
gaattcctaa gcgtcaacac cagc                                           24

<210> SEQ ID NO 17
<211> LENGTH: 19
<212> TYPE: DNA
<213> ORGANISM: Artificial sequence
<220> FEATURE:
<223> OTHER INFORMATION: Description of the artificial sequence:
      oligonucleotide (+) of insertion into pT7-7

<400> SEQUENCE: 17
catatggaat acgttgttc                                                 19

<210> SEQ ID NO 18
<211> LENGTH: 28
<212> TYPE: DNA
<213> ORGANISM: Artificial sequence
<220> FEATURE:
<223> OTHER INFORMATION: Description of the artificial sequence:
      oligonucleotide (-) of insertion into pT7-7

<400> SEQUENCE: 18
aagcttaagc ttcagcctga gagatcag                                       28

<210> SEQ ID NO 19
<211> LENGTH: 103
<212> TYPE: DNA
<213> ORGANISM: Artificial sequence
<220> FEATURE:
<223> OTHER INFORMATION: Description of the artificial sequence: sens
      DNA coding TME2 + 5' Nde I site and 3' Hind III site

<400> SEQUENCE: 19
catatggaat acgttgttct gctgttcctg ctgctggctg acgctcgtgt ttgctcttgc     60
ctgtggatga tgctgctgat ctctcaggct gaagcttaag ctt                     103

<210> SEQ ID NO 20
<211> LENGTH: 103
<212> TYPE: DNA
<213> ORGANISM: Artificial sequence
<220> FEATURE:
<223> OTHER INFORMATION: Description of the artificial sequence: sens
      DNA anticoding TME2 + 3' Nde I site and 5' Hind III site

<400> SEQUENCE: 20
aagcttaagc ttcagcctga gagatcagca gcatcatcca caggcaagag caaacacgag     60
cgtcagccag cagcaggaac agcagaacaa cgtattccat atg                     103

<210> SEQ ID NO 21
<211> LENGTH: 68
<212> TYPE: DNA
<213> ORGANISM: Artificial sequence
<220> FEATURE:
<223> OTHER INFORMATION: Description of the artificial sequence:
      sens oligonucleotide (+) coding for the synthesis
      of TME2

<400> SEQUENCE: 21
catatggaat acgttgttct gctgttcctg ctgctggctg acgctcgtgt ttgctcttgc     60
ctgtggat                                                             68

<210> SEQ ID NO 22
<211> LENGTH: 57
<212> TYPE: DNA
<213> ORGANISM: Artificial sequence
<220> FEATURE:
<223> OTHER INFORMATION: Description of the artificial sequence:
      sens oligonucleotide (-) coding for the synthesis
      of TME2

<400> SEQUENCE: 22
aagcttaagc ttcagcctga gagatcagca gcatcatcca caggcaagac gaaacac    57

<210> SEQ ID NO 23
<211> LENGTH: 19
<212> TYPE: DNA
<213> ORGANISM: Artificial sequence
<220> FEATURE:
<223> OTHER INFORMATION: Description of the artificial sequence:
      oligonucleotide (+) of insertion into pGEXKT without
      the dp site

<400> SEQUENCE: 23
ggatccgaat acgttgttc                                               19

<210> SEQ ID NO 24
<211> LENGTH: 25
<212> TYPE: DNA
<213> ORGANISM: Artificial sequence
<220> FEATURE:
<223> OTHER INFORMATION: Description of the artificial sequence:
      oligonucleotide (+) of insertion into pGEXKT with
      the dp site

<400> SEQUENCE: 24
ggatccgacc cggaatacgt tgttc                                        25

<210> SEQ ID NO 25
<211> LENGTH: 30
<212> TYPE: DNA
<213> ORGANISM: Artificial sequence
<220> FEATURE:
<223> OTHER INFORMATION: Description of the artificial sequence:
      oligonucleotide (-) of insertion into pGEXKT with
      the dp site

<400> SEQUENCE: 25
gaattcttaa gcttcagcct gagagatcag                                   30

<210> SEQ ID NO 26
<211> LENGTH: 27
<212> TYPE: DNA
<213> ORGANISM: Artificial sequence
<220> FEATURE:
<223> OTHER INFORMATION: Description of the artificial sequence:
      oligonucleotide (+) of insertion into pT7-7

<400> SEQUENCE: 26
cgcatatgga cccggaatac gttgttc                                      27

<210> SEQ ID NO 27
<211> LENGTH: 27
<212> TYPE: DNA
<213> ORGANISM: Artificial sequence
<220> FEATURE:
<223> OTHER INFORMATION: Description of the artificial sequence:
      oligonucleotide (-) of insertion into pT7-7

<400> SEQUENCE: 27

```
cagaattcct aagcttcagc ctgagag                                          27
```

<210> SEQ ID NO 28
<211> LENGTH: 15
<212> TYPE: PRT
<213> ORGANISM: Artificial sequence
<220> FEATURE:
<223> OTHER INFORMATION: Description of the artificial sequence: end
      of the GST followed by the thrombine site

<400> SEQUENCE: 28

Ser Asp Leu Ser Gly Gly Gly Gly Gly Leu Val Pro Arg Gly Ser
  1               5                  10                  15

<210> SEQ ID NO 29
<211> LENGTH: 717
<212> TYPE: DNA
<213> ORGANISM: Artificial sequence
<220> FEATURE:
<223> OTHER INFORMATION: Description of the artificial sequence: DNA
      coding for GST protein in the pGEXKT vector

<400> SEQUENCE: 29

```
atgtcccta  tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccaa tcttccttta ttatattgat     180
ggtgatgtta aattaacaca gtctatggcc atcatacgtt atatagctga caagcacaac     240
atgttgggtg ttgtccaaa  agagcgtgca gagatttcaa tgcttgaagg agcggttttg     300
gatattagat acgtgtttc  gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgtttttaaa    540 aaacgtattg aagctatccc acaaattgat aagtacttga atccagcaa  gtatatagca     600 tggcctttgc agggctggca agccacgttt ggtggtggcg accatcctcc aaaatcggat     660
ctgtctggtg gtggtggtgg tctggttccg cgtggatccc cgggaattca tcgtgac       717
```

<210> SEQ ID NO 30
<211> LENGTH: 327
<212> TYPE: DNA
<213> ORGANISM: Artificial sequence
<220> FEATURE:
<223> OTHER INFORMATION: Description of the artificial sequence: DNA
      coding for the thioredoxine in the pET32a+ vector

<400> SEQUENCE: 30

```
atgagcgata aaattattca cctgactgac gacagttttg acacggatgt actcaaagcg      60 gacgggggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggcc                                         327
```

<210> SEQ ID NO 31
<211> LENGTH: 4969
<212> TYPE: DNA
<213> ORGANISM: Artificial sequence
<220> FEATURE:
<223> OTHER INFORMATION: Description of the artificial sequence: plasmide expressing pGEXKT

<400> SEQUENCE: 31

```
acgttatcga ctgcacggtg caccaatgct tctggcgtca ggcagccatc ggaagctgtg      60
gtatggctgt gcaggtcgta atcactgca taattcgtgt cgctcaaggc gcactcccgt     120
tctggataat gtttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa agtttgaatt gggtttggag tttcccaatc     420
ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg ttttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg tctggtggtg gtggtggtct ggttccgcgt ggatccccgg     960
gaattcatcg tgactgactg acgatctgcc tcgcgcgttt cggtgatgac ggtgaaaacc    1020
tctgacacat gcagctcccg gagacggtca gcttgtctgtaagcggat gccgggagca    1080
gacaagcccg tcagggcgcg tcagcgggtg ttggcgggtg tcgggcgca gccatgaccc    1140
agtcacgtag cgatagcgga gtgtataatt cttgaagacg aaagggcctc gtgatacgcc    1200
tatttttata ggttaatgtc atgataataa tggtttctta gacgtcaggt ggcacttttc    1260
ggggaaatgt gcgcggaacc cctatttgtt tatttttcta atacattca aatatgtatc    1320
cgctcatgag acaataaccc tgataaatgc ttcaataata ttgaaaaagg aagagtatga    1380
gtattcaaca tttccgtgtc gcccttattc ccttttttgc ggcattttgc cttcctgttt    1440
ttgctcaccc agaaacgctg gtgaaagtaa aagatgctga agatcagttg ggtgcacgag    1500
tgggttacat cgaactggat ctcaacagcg gtaagatcct tgagagtttt cgccccgaag    1560
aacgttttcc aatgatgagc acttttaaag ttctgctatg tggcgcggta ttatcccgtg    1620
ttgacgccgg gcaagagcaa ctcggtcgcc gcatacacta ttctcagaat gacttggttg    1680
agtactcacc agtcacagaa aagcatctta cggatggcat gacagtaaga gaattatgca    1740
gtgctgccat aaccatgagt gataacactg cggccaactt acttctgaca acgatcggag    1800
gaccgaagga gctaaccgct tttttgcaca acatggggga tcatgtaact cgccttgatc    1860
gttgggaacc ggagctgaat gaagccatac caaacgacga gcgtgacacc acgatgcctg    1920
cagcaatggc aacaacgttg cgcaaactat taactggcga actacttact ctagcttccc    1980
ggcaacaatt aatagactgg atggaggcgg ataaagttgc aggaccactt ctgcgctcgg    2040
cccttccggc tggctggttt attgctgata aatctggagc cggtgagcgt gggtctcgcg    2100
gtatcattgc agcactgggg ccagatggta agccctcccg tatcgtagtt atctacacga    2160
cggggagtca ggcaactatg gatgaacgaa atagacagat cgctgagata ggtgcctcac    2220
```

```
tgattaagca ttggtaactg tcagaccaag tttactcata tatactttag attgatttaa    2280
aacttcattt ttaatttaaa aggatctagg tgaagatcct ttttgataat ctcatgacca    2340
aaatccctta acgtgagttt tcgttccact gagcgtcaga ccccgtagaa aagatcaaag    2400
gatcttcttg agatcctttt tttctgcgcg taatctgctg cttgcaaaca aaaaaaccac    2460
cgctaccagc ggtggtttgt ttgccggatc aagagctacc aactcttttt ccgaaggtaa    2520
ctggcttcag cagagcgcag ataccaaata ctgtccttct agtgtagccg tagttaggcc    2580
accacttcaa gaactctgta gcaccgccta catacctcgc tctgctaatc ctgttaccag    2640
tggctgctgc cagtggcgat aagtcgtgtc ttaccgggtt ggactcaaga cgatagttac    2700
cggataaggc gcagcggtcg ggctgaacgg ggggttcgtg cacacagccc agcttggagc    2760
gaacgaccta caccgaactg agatacctac agcgtgagct atgagaaagc gccacgcttc    2820
ccgaagggag aaaggcggac aggtatccgg taagcggcag ggtcggaaca ggagagcgca    2880
cgagggagct ccaggggga acgcctggt atctttatag tcctgtcggg tttcgccacc    2940
tctgacttga gcgtcgattt ttgtgatgct cgtcagggg gcggagccta tggaaaaacg    3000
ccagcaacgc ggccttttta cggttcctgg ccttttgctg gccttttgct cacatgttct    3060
ttcctgcgtt atcccctgat tctgtggata accgtattac cgcctttgag tgagctgata    3120
ccgctcgccg cagccgaacg accgagcgca gcgagtcagt gagcgaggaa gcggaagagc    3180
gcctgatgcg gtattttctc cttacgcatc tgtgcggtat ttcacaccgc ataaattccg    3240
acaccatcga atggtgcaaa acctttcgcg gtatggcatg atagcgcccg gaagagagtc    3300
aattcagggt ggtgaatgtg aaaccagtaa cgttatacga tgtcgcagag tatgccggtg    3360
tctcttatca gaccgtttcc cgcgtggtga accaggccag ccacgtttct gcgaaaacgc    3420
gggaaaaagt ggaagcggcg atggcggagc tgaattacat tcccaaccgc gtggcacaac    3480
aactggcggg caaacagtcg ttgctgattg gcgttgccac ctccagtctg gccctgcacg    3540
cgccgtcgca aattgtcgcg gcgattaaat ctcgcgccga tcaactgggt gccagcgtgg    3600
tggtgtcgat ggtagaacga agcggcgtcg aagcctgtaa agcggcggtg cacaatcttc    3660
tcgcgcaacg cgtcagtggg ctgatcatta actatccgct ggatgaccag gatgccattg    3720
ctgtggaagc tgcctgcact aatgttccgg cgttatttct tgatgtctct gaccagacac    3780
ccatcaacag tattattttc tcccatgaag acggtacgcg actgggcgtg gagcatctgg    3840
tcgcattggg tcaccagcaa atcgcgctgt tagcgggccc attaagttct gtctcggcgc    3900
gtctgcgtct ggctggctgg cataaatatc tcactcgcaa tcaaattcag ccgatagcgg    3960
aacgggaagg cgactggagt gccatgtccg gttttcaaca aaccatgcaa atgctgaatg    4020
agggcatcgt tcccactgcg atgctggttg ccaacgatca gatggcgctg ggcgcaatgc    4080
gcgccattac cgagtccggg ctgcgcgttg gtgcggatat ctcggtagtg ggatacgacg    4140
ataccgaaga cagctcatgt tatatcccgc cgttaaccac catcaaacag gattttcgcc    4200
tgctggggca aaccagcgtg gaccgcttgc tgcaactctc tcagggccag gcggtgaagg    4260
gcaatcagct gttgcccgtc tcactggtga aaagaaaaac caccctggcg cccaatacgc    4320
aaaccgcctc tccccgcgcg ttggccgatt cattaatgca gctggcacga caggtttccc    4380
gactggaaag cgggcagtga gcgcaacgca attaatgtga gttagctcac tcattaggca    4440
ccccaggctt tacactttat gcttccggct cgtatgttgt gtggaattgt gagcggataa    4500
caatttcaca caggaaacag ctatgaccat gattacggat tcactggccg tcgttttaca    4560
```

```
acgtcgtgac tgggaaaacc ctggcgttac ccaacttaat cgccttgcag cacatccccc    4620
tttcgccagc tggcgtaata gcgaagaggc ccgcaccgat cgcccttccc aacagttgcg    4680
cagcctgaat ggcgaatggc gctttgcctg gtttccggca ccagaagcgg tgccggaaag    4740
ctggctggag tgcgatcttc ctgaggccga tactgtcgtc gtcccctcaa actggcagat    4800
gcacggttac gatgcgccca tctacaccaa cgtaacctat cccattacgg tcaatccgcc    4860
gtttgttccc acgagaatcc cgacgggttg ttactcgctc acatttaatg ttgatgaaag    4920
ctggctacag gaaggccaga cgcgaattat ttttgatggc gttggaatt              4969
```

<210> SEQ ID NO 32  
<211> LENGTH: 11800  
<212> TYPE: DNA  
<213> ORGANISM: Artificial sequence  
<220> FEATURE:  
<223> OTHER INFORMATION: Description of the artificial sequence: plasmide expressing pET32a+

<400> SEQUENCE: 32

```
atccggatat agttcctcct ttcagcaaaa aaccccctcaa gacccgttta gaggccccaa      60
ggggttatgc tagttattgc tcagcggtgg cagcagccaa taggcctata tcaaggagga    120
aagtcgtttt tggggagtt ctgggcaaat ctccggggtt ccccaatacg atcaataacg    180
agtcgccacc gtcgtcggtt ctcagcttcc tttcgggctt gttagcagc cggatctcag    240 tggtggtggt ggtggtgctc gagtgcggcc gcaagcttgt cgacggagct cgaattcgga    300
gagtcgaagg aaagcccgaa acaatcgtcg gcctagagtc accaccacca ccaccacgag    360
ctcacgccgg cgttcgaaca gctgcctcga gcttaagcct tccgatatca gccatggcct    420
tgtcgtcgtc gtcggtaccc agatctgggc tgtccatgtg ctggcgttcg aatttagcag    480
cagcggtttc tttcatacca aggctatagt cggtaccgga acagcagcag cagccatggg    540
tctagacccg acaggtacac gaccgcaagc ttaaatcgtc gtcgcaaag aaagtatggt    600 gaaccgcgtg gcaccagacc agaagaatga tgatgatgat ggtgcatatg ccagaaccaa    660
gaaccggcca ggttagcgtc gaggaactct ttcaactgac cttggcgcac cgtggtctgg    720
tcttcttact actactacta ccacgtatac cggtcttggt cttggccggt ccaatcgcag    780
ctccttgaga aagttgactg ctttagacag tgcacccact tggttgccg ccacttcacc    840 gttttttgaac agcagcagag tcgggatacc acggatgcca tatttcggcg cagtgccagg    900
gaaatctgtc acgtgggtga accaacggc ggtgaagtgg caaaaacttg tcgtcgtctc    960
agccctatgg tgcctacggt ataaagccgc gtcacggtcc gttttgatcg atgttcagtt   1020
ttgcaacggt cagtttgccc tgatattcgt cagcgatttc atccagaatc ggggcgatca   1080
ttttgcacgg accgcaccac caaaactagc tacaagtcaa acgttgcca gtcaaacggg    1140 actataagca gtcgctaaag taggtcttag ccccgctagt aaaacgtgcc tggcgtggtg   1200
tctgcccaga atcgacgag gatcgccccg tccgctttga gtacatccgt gtcaaaactg   1260
tcgtcagtca ggtgaataat tttatcgctc atatgtatat agacgggtct ttagctgctc   1320 ctagcgggc aggcgaaact catgtaggca cagttttgac agcagtcagt ccacttatta   1380
aaatagcgag tatacatata ctccttctta agttaaaaca aaattatttc tagaggggaa   1440
ttgttatccg ctcacaattc ccctatagtg agtcgtatta atttcgcggg atcgagatcg   1500
gaggaagaat tcaatttgt tttaataaag atctccccctt aacaataggc gagtgttaag   1560
gggatatcac tcagcataat taaagcgccc tagctctagc atctcgatcc tctacgccgg   1620
```

```
acgcatcgtg gccggcatca ccggcgccac aggtgcggtt gctggcgcct atatcgccga   1680
catcaccgat ggggaagatc tagagctagg agatgcggcc tgcgtagcac cggccgtagt   1740
ggccgcggtg tccacgccaa cgaccgcgga tatagcggct gtagtggcta cccttctag    1800 gggctcgcca cttcgggctc atgagcgctt gtttcggcgt gggtatggtg gcaggccccg   1860
tggccggggg actgttgggc gccatctcct tgcatgcacc cccgagcggt gaagcccgag   1920
tactcgcgaa caaagccgca cccataccac cgtccggggc accggccccc tgacaacccg   1980
cggtagagga acgtacgtgg attccttgcg gcggcggtgc tcaacggcct caacctacta   2040
ctgggctgct tcctaatgca ggagtcgcat aagggagagc gtcgagatcc cggacaccat   2100
taaggaacgc cgccgccacg agttgccgga gttggatgat gacccgacga aggattacgt   2160
cctcagcgta ttccctctcg cagctctagg gcctgtggta cgaatggcgc aaaacctttc   2220
gcggtatggc atgatagcgc ccggaagaga gtcaattcag ggtggtgaat gtgaaaccag   2280
taacgttata cgatgtcgca gcttaccgcg ttttggaaag cgccataccg tactatcgcg   2340
ggccttctct cagttaagtc ccaccactta cactttggtc attgcaatat gctacagcgt   2400
gagtatgccg gtgtctctta tcagaccgtt cccgcgtgg tgaaccaggc cagccacgtt    2460
tctgcgaaaa cgcgggaaaa agtggaagcg gcgatggcgg ctcatacggc cacagagaat   2520
agtctggcaa agggcgcacc acttggtccg gtcggtgcaa agacgctttt gcgcccttt    2580 tcaccttcgc cgctaccgcc agctgaatta cattcccaac cgcgtggcac aacaactggc   2640
gggcaaacag tcgttgctga ttggcgttgc cacctccagt ctggccctgc acgcgccgtc   2700
tcgacttaat gtaagggttg gcgcaccgtg ttgttgaccg cccgtttgtc agcaacgact   2760
aaccgcaacg gtggaggtca gaccgggacg tgcgcggcag gcaaattgtc gcggcgatta   2820
aatctcgcgc cgatcaactg ggtgccagcg tggtggtgtc gatggtagaa cgaagcggcg   2880
tcgaagcctg taaagcggcg cgtttaacag cgccgctaat ttagagcgcg gctagttgac   2940
ccacggtcgc accaccacag ctaccatctt gcttcgccgc agcttcggac atttcgccgc   3000
gtgcacaatc ttctcgcgca acgcgtcagt gggctgatca ttaactatcc gctggatgac   3060
caggatgcca ttgctgtgga agctgcctgc actaatgttc cacgtgttag aagagcgcgt   3120
tgcgcagtca cccgactagt aattgatagg cgacctactg gtcctacggt aacgacacct   3180
tcgacggacg tgattacaag cggcgttatt tcttgatgtc tctgaccaga cacccatcaa   3240
cagtattatt ttctcccatg aagacggtac gcgactgggc gtggagcatc tggtcgcatt   3300
gccgcaataa agaactacag agactggtct gtgggtagtt gtcataataa agagggtac    3360 ttctgccatg cgctgacccg cacctcgtag accagcgtaa gggtcaccag caaatcgcgc   3420
tgttagcggg cccattaagt tctgtctcgg cgcgtctgcg tctggctggc tggcataaat   3480
atctcactcg caatcaaatt cccagtggtc gtttagcgcg acaatcgccc gggtaattca   3540
agacagagcc gcgcagacgc agaccgaccg accgtattta tagagtgagc gttagtttaa   3600
cagccgatag cggaacggga aggcgactgg agtgccatgt ccggttttca acaaaccatg   3660
caaatgctga atgagggcat cgttcccact gcgatgctgg gtcggctatc gccttgccct   3720
tccgctgacc tcacggtaca ggccaaaagt tgtttggtac gtttacgact tactcccgta   3780
gcaagggtga cgctacgacc ttgccaacga tcagatggcg ctgggcgcaa tgcgcgccat   3840
taccgagtcc gggctgcgcg ttggtgcgga catctcggta gtgggatacg acgataccga   3900
aacggttgct agtctaccgc gacccgcgtt acgcgcggta atggctcagg cccgacgcgc   3960
aaccacgcct gtagagccat caccctatgc tgctatggct agacagctca tgttatatcc   4020
```

-continued

```
cgccgttaac caccatcaaa caggattttc gcctgctggg gcaaaccagc gtggaccgct   4080
tgctgcaact ctctcagggc tctgtcgagt acaatatagg gcggcaattg gtggtagttt   4140
gtcctaaaag cggacgaccc cgtttggtcg cacctggcga acgacgttga gagagtcccg   4200
caggcggtga agggcaatca gctgttgccc gtctcactgg tgaaaagaaa aaccaccctg   4260
gcgcccaata cgcaaaccgc ctctccccgc gcgttggccg gtccgccact tcccgttagt   4320
cgacaacggg cagagtgacc acttttcttt ttggtgggac cgcgggttat gcgtttggcg   4380
gagaggggcg cgcaaccggc attcattaat gcagctggca cgacaggttt cccgactgga   4440
aagcgggcag tgagcgcaac gcaattaatg taagttagct cactcattag gcaccgggat   4500
taagtaatta cgtcgaccgt gctgtccaaa gggctgacct ttcgcccgtc actcgcgttg   4560
cgttaattac attcaatcga gtgagtaatc cgtggcccta ctcgaccgat gcccttgaga   4620
gccttcaacc cagtcagctc cttccggtgg gcgcggggca tgactatcgt cgccgcactt   4680
atgactgtct tctttatcat gagctggcta cgggaactct cggaagttgg gtcagtcgag   4740
gaaggccacc cgcgccccgt actgatagca gcggcgtgaa tactgacaga gaaatagta   4800
gcaactcgta ggacaggtgc cggcagcgct ctgggtcatt ttcggcgagg accgctttcg   4860
ctggagcgcg acgatgatcg gcctgtcgct tgcggtattc cgttgagcat cctgtccacg   4920
gccgtcgcga gacccagtaa aagccgctcc tggcgaaagc gacctcgcgc tgctactagc   4980
cggacagcga acgccataag ggaatcttgc acgccctcgc tcaagccttc gtcactggtc   5040
ccgccaccaa acgtttcggc gagaagcagg ccattatcgc cggcatggcg gccccacggg   5100
ccttagaacg tgcgggagcg agttcggaag cagtgaccag ggcggtggtt tgcaaagccg   5160
ctcttcgtcc ggtaatagcg gccgtaccgc cggggtgccc tgcgcatgat cgtgctcctg   5220
tcgttgagga cccggctagg ctggcggggt tgccttactg gttagcagaa tgaatcaccg   5280
atacgcgagc gaacgtgaag acgcgtacta gcacgaggac agcaactcct gggccgatcc   5340
gaccgcccca acggaatgac caatcgtctt acttagtggc tatgcgctcg cttgcacttc   5400
cgactgctgc tgcaaaacgt ctgcgacctg agcaacaaca tgaatggtct tcggtttccg   5460
tgtttcgtaa agtctggaaa cgcggaagtc agcgccctgc gctgacgacg acgttttgca   5520
gacgctggac tcgttgttgt acttaccaga agccaaaggc acaaagcatt tcagaccttt   5580
gcgccttcag tcgcgggacg accattatgt tccggatctg catcgcagga tgctgctggc   5640
taccctgtgg aacacctaca tctgtattaa cgaagcgctg gcattgaccc tgagtgattt   5700
tggtaataca aggcctagac gtagcgtcct acgacgaccg atgggacacc ttgtggatgt   5760
agacataatt gcttcgcgac cgtaactggg actcactaaa ttctctggtc ccgccgcatc   5820
cataccgcca gttgtttacc ctcacaacgt tccagtaacc gggcatgttc atcatcagta   5880
acccgtatcg tgagcatcct aagagaccag ggcggcgtag gtatggcggt caacaaatgg   5940
gagtgttgca aggtcattgg cccgtacaag tagtagtcat tgggcatagc actcgtagga   6000
ctctcgtttc atcggtatca ttaccccat gaacagaaat ccccccttaca cggaggcatc   6060
agtgaccaaa caggaaaaaa ccgcccttaa catggcccgc gagagcaaag tagccatagt   6120
aatgggggta cttgtcttta ggggaatgt gcctccgtag tcactggttt gtcctttttt   6180
ggcgggaatt gtaccgggcg tttatcagaa gccagacatt aacgcttctg gagaaactca   6240
acgagctgga cgcggatgaa caggcagaca tctgtgaatc gcttcacgac cacgctgatg   6300
aaatagtctt cggtctgtaa ttgcgaagac ctctttgagt tgctcgacct gcgcctactt   6360
```

-continued

```
gtccgtctgt agacacttag cgaagtgctg gtgcgactac agctttaccg cagctgcctc    6420
gcgcgtttcg gtgatgacgg tgaaaacctc tgacacatgc agctcccgga gacggtcaca    6480
gcttgtctgt aagcggatgc tcgaaatggc gtcgacggag cgcgcaaagc cactactgcc    6540
acttttggag actgtgtacg tcgagggcct ctgccagtgt cgaacagaca ttcgcctacg    6600
cgggagcaga caagcccgtc agggcgcgtc agcgggtgtt ggcgggtgtc ggggcgcagc    6660
catgacccag tcacgtagcg atagcggagt gtatactggc gccctcgtct gttcgggcag    6720
tcccgcgcag tcgcccacaa ccgcccacag ccccgcgtcg gtactgggtc agtgcatcgc    6780
tatcgcctca catatgaccg ttaactatgc ggcatcagag cagattgtac tgagagtgca    6840
ccatatatgc ggtgtgaaat accgcacaga tgcgtaagga gaaataccg catcaggcgc     6900
aattgatacg ccgtagtctc gtctaacatg actctcacgt ggtatatacg ccacacttta    6960
tggcgtgtct acgcattcct ctttatggc gtagtccgcg tcttccgctt cctcgctcac     7020
tgactcgctg cgctcggtcg ttcggctgcg gcgagcggta tcagctcact caaaggcggt    7080
aatacggtta tccacagaat agaaggcgaa ggagcgagtg actgagcgac gcgagccagc    7140
aagccgacgc cgctcgccat agtcgagtga gtttccgcca ttatgccaat aggtgtctta    7200
caggggataa cgcaggaaag aacatgtgag caaaaggcca gcaaaaggcc aggaaccgta    7260
aaaaggccgc gttgctggcg ttttccata ggctccgccc gtccctatt cgtcctttc      7320
ttgtacactc gttttccggt cgttttccgg tccttggcat ttttccggcg caacgaccgc    7380
aaaaaggtat ccgaggcggg ccctgacgag catcacaaaa atcgacgctc aagtcagagg    7440
tggcgaaacc cgacaggact ataaagatac caggcgtttc ccctggaag ctccctcgtg     7500
gggactgctc gtagtgtttt tagctgcgag ttcagtctcc accgctttgg ctgtcctga    7560
tatttctatg gtccgcaaag ggggaccttc gagggagcac cgctctcctg ttccgaccct    7620
gccgcttacc ggatacctgt ccgcctttct cccttcggga agcgtggcgc tttctcatag    7680
ctcacgctgt aggtatctca gcgagaggac aaggctggga cggcgaatgg cctatggaca    7740
ggcgaaaga gggaagccct tcgcaccgcg aaagagtatc gagtgcgaca tccatagagt     7800
gttcggtgta ggtcgttcgc tccaagctgg gctgtgtgca cgaacccccc gttcagcccg    7860
accgctgcgc cttatccggt aactatcgtc ttgagtccaa caagccacat ccagcaagcg    7920
aggttcgacc cgacacacgt gcttgggggg caagtcgggc tggcgacgcg gaataggcca    7980
ttgatagcag aactcaggtt cccggtaaga cacgacttat cgccactggc agcagccact    8040
ggtaacagga ttagcagagc gaggtatgta ggcggtgcta cagagttctt gaagtggtgg    8100
gggccattct gtgctgaata gcggtgaccg tcgtcggtga ccattgtcct aatcgtctcg    8160
ctccatacat ccgccacgat gtctcaagaa cttcaccacc cctaactacg gctacactag    8220
aaggacagta tttggtatct gcgctctgct gaagccagtt accttcggaa aaagagttgg    8280
tagctcttga tccggcaaac ggattgatgc cgatgtgatc ttcctgtcat aaaccataga    8340
cgcgagacga cttcggtcaa tggaagcctt tttctcaacc atcgagaact aggccgtttg    8400
aaaccaccgc tggtagcggt ggtttttttg tttgcaagca gcagattacg cgcagaaaaa    8460
aaggatctca agaagatcct ttgatctttt ctacggggtc tttggtggcg accatcgcca    8520
ccaaaaaaac aaacgttcgt cgtctaatgc gcgtcttttt ttcctagagt tcttctagga    8580
aactagaaaa gatgccccag tgacgctcag tggaacgaaa actcacgtta agggatttg     8640
gtcatgagat tatcaaaaag gatcttcacc tagatccttt taaattaaaa atgaagtttt    8700
actgcgagtc accttgcttt tgagtgcaat tccctaaaac cagtactcta atagttttc     8760
```

```
ctagaagtgg atctaggaaa atttaatttt tacttcaaaa aaatcaatct aaagtatata   8820
tgagtaaact tggtctgaca gttaccaatg cttaatcagt gaggcaccta tctcagcgat   8880
ctgtctattt cgttcatcca tttagttaga tttcatatat actcatttga accagactgt   8940
caatggttac gaattagtca ctccgtggat agagtcgcta gacagataaa gcaagtaggt   9000
tagttgcctg actccccgtc gtgtagataa ctacgatacg ggagggctta ccatctggcc   9060
ccagtgctgc aatgataccg cgagacccac gctcaccggc atcaacggac tgaggggcag   9120
cacatctatt gatgctatgc cctcccgaat ggtagaccgg ggtcacgacg ttactatggc   9180
gctctgggtg cgagtggccg tccagattta tcagcaataa accagccagc cggaagggcc   9240
gagcgcagaa gtggtcctgc aactttatcc gcctccatcc agtctattaa ttgttgccgg   9300
aggtctaaat agtcgttatt tggtcggtcg gccttcccgg ctcgcgtctt caccaggacg   9360
ttgaaatagg cggaggtagg tcagataatt aacaacggcc gaagctagag taagtagttc   9420
gccagttaat agtttgcgca acgttgttgc cattgctgca ggcatcgtgg tgtcacgctc   9480
gtcgtttggt atggcttcat cttcgatctc attcatcaag cggtcaatta tcaaacgcgt   9540
tgcaacaacg gtaacgacgt ccgtagcacc acagtgcgag cagcaaacca taccgaagta   9600
tcagctccgg ttcccaacga tcaaggcgag ttacatgatc ccccatgttg tgcaaaaaag   9660
cggttagctc cttcggtcct ccgatcgttg tcagaagtaa agtcgaggcc aagggttgct   9720
agttccgctc aatgtactag ggggtacaac acgttttttc gccaatcgag gaagccagga   9780
ggctagcaac agtcttcatt gttggccgca gtgttatcac tcatggttat ggcagcactg   9840
cataattctc ttactgtcat gccatccgta agatgctttt ctgtgactgg tgagtactca   9900
caaccggcgt cacaatagtg agtaccaata ccgtcgtgac gtattaagag aatgacagta   9960
cggtaggcat tctacgaaaa gacactgacc actcatgagt accaagtcat tctgagaata  10020
gtgtatgcgc cgaccgagtt gctcttgccc ggcgtcaata cgggataata ccgcgccaca  10080
tagcagaact ttaaaagtgc tggttcagta agactcttat cacatacgcc gctggctcaa  10140
cgagaacggg ccgcagttat gccctattat ggcgcggtgt atcgtcttga aattttcacg  10200
tcatcattgg aaaacgttct tcggggcgaa aactctcaag gatcttaccg ctgttgagat  10260
ccagttcgat gtaacccact cgtgcaccca actgatcttc agtagtaacc ttttgcaaga  10320
agccccgctt ttgagagttc ctagaatggc gacaactcta ggtcaagcta cattgggtga  10380
gcacgtgggt tgactagaag agcatctttt actttcacca gcgtttctgg gtgagcaaaa  10440
acaggaaggc aaaatgccgc aaaaaaggga ataagggcga cacggaaatg ttgaatactc  10500
tcgtagaaaa tgaaagtggt cgcaaagacc cactcgtttt tgtccttccg ttttacggcg  10560
ttttttccct tattcccgct gtgcctttac aacttatgag atactcttcc tttttcaata  10620
ttattgaagc atttatcagg gttattgtct catgagcgga tacatatttg aatgtattta  10680
gaaaaataaa caaataggg tatgagaagg aaaaagttat aataacttcg taaatagtcc  10740
caataacaga gtactcgcct atgtataaac ttacataaat ctttttattt gtttatcccc  10800
ttccgcgcac atttccccga aaagtgccac ctgaaattgt aaacgttaat attttgttaa  10860
aattcgcgtt aaatttttgt taaatcagct catttttaa aaggcgcgtg taaagggct   10920 tttcacggtg gactttaaca tttgcaatta taaacaatt ttaagcgcaa tttaaaaaca  10980
atttagtcga gtaaaaaatt ccaataggcc gaaatcggca aaatccctta taaatcaaaa  11040
gaatagaccg agatagggtt gagtgttgtt ccagtttgga acaagagtcc actattaaag  11100
```

```
ggttatccgg ctttagccgt tttagggaat atttagtttt cttatctggc tctatcccaa   11160
ctcacaacaa ggtcaaacct tgttctcagg tgataatttc aacgtggact ccaacgtcaa   11220
agggcgaaaa accgtctatc agggcgatgg cccactacgt gaaccatcac cctaatcaag   11280
ttttttgggg tcgaggtgcc ttgcacctga ggttgcagtt tcccgctttt tggcagatag   11340
tcccgctacc gggtgatgca cttggtagtg ggattagttc aaaaaacccc agctccacgg   11400
gtaaagcact aaatcggaac cctaaaggga gcccccgatt tagagcttga cggggaaagc   11460
cggcgaacgt ggcgagaaag gaagggaaga aagcgaaagg catttcgtga tttagccttg   11520
ggatttccct cggggcctaa atctcgaact gccccttcg gccgcttgca ccgctctttc   11580
cttcccttct ttcgctttcc agcgggcgct agggcgctgg caagtgtagc ggtcacgctg   11640
cgcgtaacca ccacacccgc cgcgcttaat gcgccgctac agggcgcgtc ccattcgcca   11700
tcgcccgcga tcccgcgacc gttcacatcg ccagtgcgac gcgcattggt ggtgtgggcg   11760
gcgcgaatta cgcggcgatg tcccgcgcag ggtaagcggt                         11800

<210> SEQ ID NO 33
<211> LENGTH: 2504
<212> TYPE: DNA
<213> ORGANISM: Artificial sequence
<220> FEATURE:
<223> OTHER INFORMATION: Description of the artificial sequence:
      plasmide expressing pT7-7

<400> SEQUENCE: 33
aattctcatg tttgacagct tatcatcgat gataagcttg ggctgcaggt cgactctaga     60
ggatccccgg gcgcgaattc tagccatatg tatatctcct tcttaaagtt aaacaaaatt    120
atttctagag ggaaaccgtt gtggtctccc tatagtgagt cgtattaatt tcgaagtcta    180
tcagaagttc gaatcgctgg gcctcgcgcg tttcggtgat gacggtgaaa acctctgaca    240
catgcagctc ccggagacgg tcacagcttg tctgtaagcg gatgccggga gcagacaagc    300
ccgtcagggc gcgtcagcgg gtgttggcgg gtgtcggggc gcagccatga cccagtcacg    360
tagcgatagc ggagtgtata tactggctta actatgcggc atcagagcag attgtactga    420
gagtgcacca taggaagatc ttccggaaga tcttcctatg cggtgtgaaa taccgcacag    480
atgcgtaagg agaaaatacc gcatcaggcg ctcttccgct tcctcgctca ctgactcgct    540
gcgctcggtc gttcggctgc ggcgagcggt atcagctcac tcaaaggcgg taatacggtt    600
atccacagaa tcaggggata acgcaggaaa gaacatgtga gcaaaaggcc agcaaaaggc    660
caggaaccgt aaaaaggccg cgttgctggc gttttccat aggctccgcc cccctgacga    720
gcatcacaaa aatcgacgct caagtcagag gtggcgaaac ccgacaggac tataaagata    780
ccaggcgttt ccccctggaa gctccctcgt gcgctctcct gttccgaccc tgccgcttac    840
cggatacctg tccgcctttc tcccttcggg aagcgtggcg ctttctcaat gctcacgctg    900
taggtatctc agttcggtgt aggtcgttcg ctccaagctg ggctgtgtgc acgaaccccc    960
cgttcagccc gaccgctgcg ccttatccgg taactatcgt cttgagtcca acccggtaag   1020
acacgactta tcgccactgg cagcagccac tggtaacagg attagcagag cgaggtatgt   1080
aggcggtgct acagagttct tgaagtggtg gcctaactac ggctacacta aggacagt    1140 atttggtatc tgcgctctgc tgaagccagt taccttcgga aaaagagttg gtagctcttg   1200
atccggcaaa caaccaccg ctggtagcgg tggtttttttt gtttgcaagc agcagattac   1260
gcgcagaaaa aaggatctc aagaagatcc tttgatcttt tctacggggt ctgacgctca   1320
```

```
gtggaacgaa aactcacgtt aagggatttt ggtcatgaga ttatcaaaaa ggatcttcac    1380
ctagatcctt ttaattcttg aagacgaaag ggcctcgtga tacgcctatt tttataggtt    1440
aatgtcatga taataatggt ttcttagacg tcaggtggca cttttcgggg aaatgtgcgc    1500 ggaacccta  tttgtttatt tttctaaata cattcaaata tgtatccgct catgagacaa    1560
taaccctgat aaatgcttca ataatattga aaaggaaga  gtatgagtat tcaacatttc    1620
cgtgtcgccc ttattccctt ttttgcggca ttttgccttc ctgttttgc  tcacccagaa    1680 acgctggtga agtaaaaga  tgctgaagat cagttgggtg cacgagtggg ttacatcgaa    1740
ctggatctca acagcggtaa gatccttgag agttttcgcc ccgaagaacg ttttccaatg    1800
atgagcactt ttaaagttct gctatgtggc gcggtattat cccgtgttga cgccgggcaa    1860
gagcaactcg gtcgccgcat acactattct cagaatgact tggttgagta ctcaccagtc    1920
acagaaaagc atcttacgga tggcatgaca gtaagagaat tatgcagtgc tgccataacc    1980
atgagtgata acactgcggc caacttactt ctgacaacga tcggaggacc gaaggagcta    2040
accgcttttt tgcacaacat gggggatcat gtaactcgcc ttgatcgttg ggaaccggag    2100
ctgaatgaag ccataccaaa cgacgagcgt gacaccacga tgcctgtagc aatggcaaca    2160
acgttgcgca aactattaac tggcgaacta cttactctag cttcccggca acaattaata    2220
gactggatgg aggcggataa agttgcagga ccacttctgc gctcggccct tccggctggc    2280
tggtttattg ctgataaatc tggagccggt gagcgtgggt ctcgcggtat cattgcagca    2340
ctggggccag atggtaagcc ctcccgtatc gtagttatct acacgacggg gagtcaggca    2400
actatggatg aacgaaatag acagatcgct gagataggtg cctcactgat taagcattgg    2460
taactgtcag accaagttta ctcatatata ctttagattg attt                     2504

<210> SEQ ID NO 34
<211> LENGTH: 813
<212> TYPE: DNA
<213> ORGANISM: Artificial sequence
<220> FEATURE:
<223> OTHER INFORMATION: Description of the artificial sequence:
      expression system coding for fusion protein GST-DP-TME1

<400> SEQUENCE: 34 atgtcccta  tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg ttgtccaaa  agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgtttaaa     540 aaacgtattg aagctatccc acaaattgat aagtacttga atccagcaa  gtatatagca     600 tggcctttgc agggctggca agccacgttt ggtggtggcg accatcctcc aaaatcggat     660
ctgtctggtg gtgtggtgg  tctggttccg cgtggatccg acccgatcgc tggtgctcac     720
tggggtgttc tggctggtat cgcttacttc tctatggttg gtaactgggc taaagttctg     780
gttgttctgc tgctgttcgc tggtgttgac gct                                 813
```

<210> SEQ ID NO 35
<211> LENGTH: 513
<212> TYPE: DNA
<213> ORGANISM: Artificial sequence
<220> FEATURE:
<223> OTHER INFORMATION: Description of the artificial sequence:
      expression system coding for fusion protein TrX-DP-TME1

<400> SEQUENCE: 35

```
atgagcgata aaattattca cctgactgac gacagttttg acacggatgt actcaaagcg      60
gacggggcga tcctcgtcga tttctgggca gagtggtgcg gtccgtgcaa atgatcgcc     120 ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg atctccaaa atcggatctg    360 tctggtggtg gtggtggtct ggttccgcgt ggatccgacc cgatcgctgg tgctcactgg    420
ggtgttctgg ctggtatcgc ttacttctct atggttggta actgggctaa agttctggtt    480
gttctgctgc tgttcgctgg tgttgacgct tag                                  513
```

<210> SEQ ID NO 36
<211> LENGTH: 117
<212> TYPE: DNA
<213> ORGANISM: Artificial sequence
<220> FEATURE:
<223> OTHER INFORMATION: Description of the artificial sequence:
      expression system coding for fusion protein M-DP-TME1

<400> SEQUENCE: 36

```
atggacccga tcgctggtgc tcactggggt gttctggctg gtatcgctta cttctctatg      60
gttggtaact gggctaaagt tctggttgtt ctgctgctgt tcgctggtgt tgacgct      117
```

<210> SEQ ID NO 37
<211> LENGTH: 795
<212> TYPE: DNA
<213> ORGANISM: Artificial sequence
<220> FEATURE:
<223> OTHER INFORMATION: Description of the artificial sequence:
      expression system coding for fusion protein
      GST-DP-TME2

<400> SEQUENCE: 37

```
atgtcccta tactaggtta ttggaaaatt aagggccttg tgcaacccac tcgacttctt       60
ttggaatatc ttgaagaaaa atatgaagag catttgtatg agcgcgatga aggtgataaa    120
tggcgaaaca aaaagtttga attgggtttg gagtttccca tcttcctta ttatattgat    180 ggtgatgtta aattaacaca gtctatggcc atcatacgtt atatagctga caagcacaac    240
atgttgggtg gttgtccaaa agagcgtgca gagatttcaa tgcttgaagg gcggttttg     300 gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctgtctggtg gtggtggtgg tctggttccg cgtggatccg acccgaata cgttgttctg    720
```
ctgttcctgc tgctggctga cgctcgtgtt tgctcttgcc tgtggatgat gctgctgatc    780
tctcaggctg aagct                                                    795

<210> SEQ ID NO 38
<211> LENGTH: 486
<212> TYPE: DNA
<213> ORGANISM: Artificial sequence
<220> FEATURE:
<223> OTHER INFORMATION: Description of the artificial sequence:
      expression system coding for fusion protein
      TrX-DP-TME2

<400> SEQUENCE: 38
atgagcgata aaattattca cctgactgac gacagttttg acacggatgt actcaaagcg     60
gacggggcga tcctcgtcga tttctgggca gagtggtgcg gtccgtgcaa aatgatcgcc    120
ccgattctgg atgaaatcgc tgacgaatat cagggcaaac tgaccgttgc aaaactgaac    180
atcgatcaaa accctggcac tgcgccgaaa tatggcatcc gtggtatccc gactctgctg    240
ctgttcaaaa acggtgaagt ggcggcaacc aaagtgggtg cactgtctaa aggtcagttg    300
aaagagttcc tcgacgctaa cctggccggt tctggttctg atctgatct gtctggtggt    360 ggtggtggtc tggttccgcg tggatccgac ccggaatacg ttgttctgct gttcctgctg    420
ctggctgacg ctcgtgtttg ctcttgcctg tggatgatgc tgctgatctc tcaggctgaa    480
gcttag                                                              486

<210> SEQ ID NO 39
<211> LENGTH: 99
<212> TYPE: DNA
<213> ORGANISM: Artificial sequence
<220> FEATURE:
<223> OTHER INFORMATION: Description of the artificial sequence:
    expression system coding for fusion protein M-DP-TME2

<400> SEQUENCE: 39
atggacccgg aatacgttgt tctgctgttc ctgctgctgg ctgacgctcg tgtttgctct     60
tgcctgtgga tgatgctgct gatctctcag gctgaagct                           99

<210> SEQ ID NO 40
<211> LENGTH: 5082
<212> TYPE: DNA
<213> ORGANISM: Artificial sequence
<220> FEATURE:
<223> OTHER INFORMATION: Description of the artificial sequence:
    expression vector pGEXKT-dp-Pt(TME1)

<400> SEQUENCE: 40
acgttatcga ctgcacggtg caccaatgct tctggcgtca ggcagccatc ggaagctgtg     60
gtatggctgt gcaggtcgta atcactgca taattcgtgt cgctcaaggc gcactcccgt    120
tctggataat gttttttgcg ccgacatcat aacggttctg gcaaatattc tgaaatgagc    180
tgttgacaat taatcatcgg ctcgtataat gtgtggaatt gtgagcggat aacaatttca    240
cacaggaaac agtattcatg tcccctatac taggttattg gaaaattaag ggccttgtgc    300
aacccactcg acttcttttg gaatatcttg aagaaaaata tgaagagcat ttgtatgagc    360
gcgatgaagg tgataaatgg cgaaacaaaa agtttgaatt gggtttggag tttcccaatc    420
ttccttatta tattgatggt gatgttaaat taacacagtc tatggccatc atacgttata    480
tagctgacaa gcacaacatg ttgggtggtt gtccaaaaga gcgtgcagag atttcaatgc    540

```
ttgaaggagc ggttttggat attagatacg gtgtttcgag aattgcatat agtaaagact    600
ttgaaactct caaagttgat tttcttagca agctacctga aatgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg cctttgcagg gctggcaagc cacgtttggt ggtggcgacc    900
atcctccaaa atcggatctg tctggtggtg gtggtggtct ggttccgcgt ggatccgacc    960
cgatcgctgg tgctcactgg ggtgttctgg ctggtatcgc ttacttctct atggttggta   1020
actgggctaa agttctggtt gttctgctgc tgttcgctgg tgttgacgct taggaattca   1080
tcgtgactga ctgacgatct gcctcgcgcg tttcggtgat gacggtgaaa acctctgaca   1140
catgcagctc ccggagacgg tcacagcttg tctgtaagcg gatgccggga gcagacaagc   1200
ccgtcagggc gcgtcagcgg gtgttggcgg gtgtcgggc gcagccatga cccagtcacg    1260
tagcgatagc ggagtgtata attcttgaag acgaaagggc ctcgtgatac gcctatttt   1320 ataggttaat gtcatgataa taatggtttc ttagacgtca ggtggcactt ttcggggaaa   1380
tgtgcgcgga accctatt tgtttatttt ctaaatacat tcaaatatgt atccgctcat    1440
gagacaataa ccctgataaa tgcttcaata atattgaaaa aggaagagta tgagtattca   1500
acatttccgt gtcgccctta ttccttttt tgcggcattt tgccttcctg ttttgctca    1560 cccagaaacg ctggtgaaag taaaagatgc tgaagatcag ttgggtgcac gagtgggtta   1620
catcgaactg gatctcaaca gcggtaagat ccttgagagt tttcgccccg aagaacgttt   1680
tccaatgatg agcactttta aagttctgct atgtggcgcg gtattatccc gtgttgacgc   1740
cgggcaagag caactcggtc gccgcataca ctattctcag aatgacttgg ttgagtactc   1800
accagtcaca gaaaagcatc ttacggatgg catgacagta agagaattat gcagtgctgc   1860
cataaccatg agtgataaca ctgcggccaa cttacttctg acaacgatcg gaggaccgaa   1920
ggagctaacc gcttttttgc acaacatggg ggatcatgta actcgccttg atcgttggga   1980
accggagctg aatgaagcca taccaaacga cgagcgtgac accacgatgc ctgcagcaat   2040
ggcaacaacg ttgcgcaaac tattaactgg cgaactactt actctagctt cccggcaaca   2100
attaatagac tggatggagg cggataaagt tgcaggacca cttctgcgct cggcccttcc   2160
ggctggctgg tttattgctg ataaatctgg agccggtgag cgtgggtctc gcggtatcat   2220
tgcagcactg gggccagatg gtaagccctc ccgtatcgta gttatctaca cgacggggag   2280
tcaggcaact atggatgaac gaaatagaca gatcgctgag ataggtgcct cactgattaa   2340
gcattggtaa ctgtcagacc aagtttactc atatatactt tagattgatt taaaacttca   2400
tttttaattt aaaaggatct aggtgaagat cctttttgat aatctcatga ccaaaatccc   2460
ttaacgtgag ttttcgttcc actgagcgtc agaccccgta gaaaagatca aaggatcttc   2520
ttgagatcct ttttttctgc gcgtaatctg ctgcttgcaa acaaaaaaac caccgctacc   2580
agcggtggtt tgtttgccgg atcaagagct accaactctt tttccgaagg taactggctt   2640
cagcagagcg cagataccaa atactgtcct tctagtgtag ccgtagttag gccaccactt   2700
caagaactct gtagcaccgc ctacatacct cgctctgcta atcctgttac cagtggctgc   2760
tgccagtggc gataagtcgt gtcttaccgg gttggactca agacgatagt taccggataa   2820
ggcgcagcgg tcgggctgaa cggggggttc gtgcacacag cccagcttgg agcgaacgac   2880
ctacaccgaa ctgagatacc tacagcgtga gctatgagaa agcgccacgc ttcccgaagg   2940
```

| | |
|---|---|
| gagaaaggcg acaggtatc cggtaagcgg cagggtcgga acaggagagc gcacgaggga | 3000 |
| gcttccaggg ggaaacgcct ggtatcttta tagtcctgtc gggtttcgcc acctctgact | 3060 |
| tgagcgtcga tttttgtgat gctcgtcagg ggggcggagc ctatggaaaa acgccagcaa | 3120 |
| cgcggccttt ttacggttcc tggccttttg ctggcttttt gctcacatgt tctttcctgc | 3180 |
| gttatcccct gattctgtgg ataaccgtat taccgccttt gagtgagctg ataccgctcg | 3240 |
| ccgcagccga acgaccgagc gcagcgagtc agtgagcgag gaagcggaag agcgcctgat | 3300 |
| gcggtatttt ctccttacgc atctgtgcgg tatttcacac cgcataaatt ccgacaccat | 3360 |
| cgaatggtgc aaaacctttc gcggtatggc atgatagcgc ccggaagaga gtcaattcag | 3420 |
| ggtggtgaat gtgaaaccag taacgttata cgatgtcgca gagtatgccg gtgtctctta | 3480 |
| tcagaccgtt tcccgcgtgg tgaaccaggc cagccacgtt tctgcgaaaa cgcgggaaaa | 3540 |
| agtggaagcg gcgatggcgg agctgaatta cattcccaac cgcgtggcac aacaactggc | 3600 |
| gggcaaacag tcgttgctga ttggcgttgc cacctccagt ctggccctgc acgcgccgtc | 3660 |
| gcaaattgtc gcggcgatta aatctcgcgc cgatcaactg ggtgccagcg tggtggtgtc | 3720 |
| gatggtagaa cgaagcggcg tcgaagcctg taaagcggcg gtgcacaatc ttctcgcgca | 3780 |
| acgcgtcagt gggctgatca ttaactatcc gctggatgac caggatgcca ttgctgtgga | 3840 |
| agctgcctgc actaatgttc cggcgttatt tcttgatgtc tctgaccaga cacccatcaa | 3900 |
| cagtattatt ttctcccatg aagacggtac gcgactgggc gtggagcatc tggtcgcatt | 3960 |
| gggtcaccag caaatcgcgc tgttagcggg cccattaagt tctgtctcgg cgcgtctgcg | 4020 |
| tctggctggc tggcataaat atctcactcg caatcaaatt cagccgatag cggaacggga | 4080 |
| aggcgactgg agtgccatgt ccggttttca acaaaccatg caaatgctga atgagggcat | 4140 |
| cgttcccact gcgatgctgg ttgccaacga tcagatggcg ctgggcgcaa tgcgcgccat | 4200 |
| taccgagtcc gggctgcgcg ttggtgcgga tatctcggta gtgggatacg acgataccga | 4260 |
| agacagctca tgttatatcc cgccgttaac caccatcaaa caggattttc gcctgctggg | 4320 |
| gcaaaccagc gtggaccgct tgctgcaact ctctcagggc caggcggtga agggcaatca | 4380 |
| gctgttgccc gtctcactgg tgaaaagaaa aaccaccctg gcgcccaata cgcaaaccgc | 4440 |
| ctctccccgc gcgttggccg attcattaat gcagctggca cgacaggttt cccgactgga | 4500 |
| aagcgggcag tgagcgcaac gcaattaatg tgagttagct cactcattag gcaccccagg | 4560 |
| ctttacactt tatgcttccg gctcgtatgt tgtgtggaat tgtgagcgga taacaatttc | 4620 |
| acacaggaaa cagctatgac catgattacg gattcactgg ccgtcgtttt acaacgtcgt | 4680 |
| gactgggaaa accctggcgt tacccaactt aatcgccttg cagcacatcc ccctttcgcc | 4740 |
| agctggcgta atagcgaaga ggcccgcacc gatcgccctt cccaacagtt gcgcagcctg | 4800 |
| aatggcgaat ggcgctttgc ctggtttccg gcaccagaag cggtgccgga agctggctg | 4860 |
| gagtgcgatc ttcctgaggc cgatactgtc gtcgtcccct caaactggca gatgcacggt | 4920 |
| tacgatgcgc ccatctacac caacgtaacc tatcccatta cggtcaatcc gccgtttgtt | 4980 |
| cccacggaga atccgacggg ttgttactcg ctcacattta atgttgatga agctggcta | 5040 |
| caggaaggcc agacgcgaat tatttttgat ggcgttggaa tt | 5082 |

<210> SEQ ID NO 41
<211> LENGTH: 5064
<212> TYPE: DNA
<213> ORGANISM: Artificial sequence
<220> FEATURE:

<223> OTHER INFORMATION: Description of the artificial sequence: expression vector pGEXKT-dp-Pt(TME2)

<400> SEQUENCE: 41

```
acgttatcga ctgcacggtg caccaatgct tctggcgtca ggcagccatc ggaagctgtg      60
gtatggctgt gcaggtcgta atcactgca taattcgtgt cgctcaaggc gcactcccgt     120
tctggataat gttttttgcg ccgacatcat aacggttctg gcaaatattc tgaaatgagc     180
tgttgacaat taatcatcgg ctcgtataat gtgtggaatt gtgagcggat aacaatttca     240
cacaggaaac agtattcatg tcccctatac taggttattg gaaaattaag ggccttgtgc     300
aacccactcg acttcttttg gaatatcttg aagaaaaata tgaagagcat ttgtatgagc     360
gcgatgaagg tgataaatgg cgaaacaaaa agtttgaatt gggtttggag tttcccaatc     420
ttccttatta tattgatggt gatgttaaat taacacagtc tatggccatc atacgttata     480
tagctgacaa gcacaacatg ttgggtggtt gtccaaaaga gcgtgcagag atttcaatgc     540
ttgaaggagc ggttttggat attagatacg gtgtttcgag aattgcatat agtaaagact     600
ttgaaactct caaagttgat tttcttagca agctacctga aatgctgaaa atgttcgaag     660
atcgtttatg tcataaaaca tatttaaatg gtgatcatgt aacccatcct gacttcatgt     720
tgtatgacgc tcttgatgtt gttttataca tggacccaat gtgcctggat gcgttcccaa     780
aattagtttg tttaaaaaa cgtattgaag ctatcccaca aattgataag tacttgaaat     840
ccagcaagta tatagcatgg cctttgcagg gctggcaagc cacgtttggt ggtggcgacc     900
atcctccaaa atcggatctg tctggtggtg gtggtggtct ggttccgcgt ggatccgacc     960
cggaatacgt tgttctgctg ttcctgctgc tggctgacgc tcgtgtttgc tcttgcctgt    1020
ggatgatgct gctgatctct caggctgaag cttaggaatt catcgtgact gactgacgat    1080
ctgcctcgcg cgtttcggtg atgacggtga aaacctctga cacatgcagc tcccggagac    1140
ggtcacagct tgtctgtaag cggatgccgg gagcagacaa gcccgtcagg gcgcgtcagc    1200
gggtgttggc gggtgtcggg gcgcagccat gacccagtca cgtagcgata gcggagtgta    1260
taattcttga agacgaaagg gcctcgtgat acgcctattt ttataggtta atgtcatgat    1320
aataatggtt tcttagacgt caggtggcac ttttcgggga atgtgcgcg gaacccctat    1380
ttgtttattt ttctaaatac attcaaatat gtatccgctc atgagacaat aaccctgata    1440
aatgcttcaa taatattgaa aaaggaagag tatgagtatt caacatttcc gtgtcgccct    1500
tattcccttt tttgcggcat tttgccttcc tgttttgct cacccagaaa cgctggtgaa    1560
agtaaaagat gctgaagatc agttgggtgc acgagtgggt tacatcgaac tggatctcaa    1620
cagcggtaag atccttgaga gttttcgccc cgaagaacgt tttccaatga tgagcacttt    1680
taaagttctg ctatgtggcg cggtattatc ccgtgttgac gccgggcaag agcaactcgg    1740
tcgccgcata cactattctc agaatgactt ggttgagtac tcaccagtca cagaaaagca    1800
tcttacggat ggcatgacag taagagaatt atgcagtgct gccataacca tgagtgataa    1860
cactgcggcc aacttacttc tgacaacgat cggaggaccg aaggagctaa ccgcttttt    1920
gcacaacatg ggggatcatg taactcgcct tgatcgttgg gaaccggagc tgaatgaagc    1980
cataccaaac gacgagcgtg acaccacgat gcctgcagca atggcaacaa cgttgcgcaa    2040
actattaact ggcgaactac ttactctagc ttcccggcaa caattaatag actggatgga    2100
ggcggataaa gttgcaggac cacttctgcg ctcggccctt ccggctggct ggtttattgc    2160
tgataaatct ggagccggtg agcgtgggtc tcgcggtatc attgcagcac tggggccaga    2220
```

```
tggtaagccc tcccgtatcg tagttatcta cacgacgggg agtcaggcaa ctatggatga    2280
acgaaataga cagatcgctg agataggtgc ctcactgatt aagcattggt aactgtcaga    2340
ccaagtttac tcatatatac tttagattga tttaaaactt catttttaat ttaaaaggat    2400
ctaggtgaag atcctttttg ataatctcat gaccaaaatc ccttaacgtg agttttcgtt    2460
ccactgagcg tcagacccccg tagaaaagat caaaggatct tcttgagatc ctttttttct    2520
gcgcgtaatc tgctgcttgc aaacaaaaaa accaccgcta ccagcggtgg tttgtttgcc    2580
ggatcaagag ctaccaactc tttttccgaa ggtaactggc ttcagcagag cgcagatacc    2640
aaatactgtc cttctagtgt agccgtagtt aggccaccac ttcaagaact ctgtagcacc    2700
gcctacatac ctcgctctgc taatcctgtt accagtggct gctgccagtg gcgataagtc    2760
gtgtcttacc gggttggact caagacgata gttaccggat aaggcgcagc ggtcgggctg    2820 aacgggggt tcgtgcacac agcccagctt ggagcgaacg acctacaccg aactgagata    2880
cctacagcgt gagctatgag aaagcgccac gcttcccgaa gggagaaagg cggacaggta    2940
tccggtaagc ggcagggtcg gaacaggaga gcgcacgagg gagcttccag ggggaaacgc    3000
ctggtatctt tatagtcctg tcgggtttcg ccacctctga cttgagcgtc gatttttgtg    3060
atgctcgtca ggggggcgga gcctatggaa aaacgccagc aacgcggcct ttttacggtt    3120
cctggccttt tgctggcctt ttgctcacat gttctttcct gcgttatccc ctgattctgt    3180
ggataaccgt attaccgcct ttgagtgagc tgataccgct cgccgcagcc gaacgaccga    3240
gcgcagcgag tcagtgagcg aggaagcgga agagcgcctg atgcggtatt ttctccttac    3300
gcatctgtgc ggtatttcac accgcataaa ttccgacacc atcgaatggt gcaaaacctt    3360
tcgcggtatg gcatgatagc gcccggaaga gagtcaattc agggtggtga atgtgaaacc    3420
agtaacgtta tacgatgtcg cagagtatgc cggtgtctct tatcagaccg tttcccgcgt    3480
ggtgaaccag gccagccacg tttctgcgaa aacgcgggaa aaagtggaag cggcgatggc    3540
ggagctgaat tacattccca accgcgtggc acaacaactg gcgggcaaac agtcgttgct    3600
gattggcgtt gccacctcca gtctggccct gcacgcgccg tcgcaaattg tcgcggcgat    3660
taaatctcgc gccgatcaac tgggtgccag cgtggtggtg tcgatggtag aacgaagcgg    3720
cgtcgaagcc tgtaaagcgg cggtgcacaa tcttctcgcg caacgcgtca gtgggctgat    3780
cattaactat ccgctggatg accaggatgc cattgctgtg gaagctgcct gcactaatgt    3840
tccggcgtta tttcttgatg tctctgacca gacacccatc aacagtatta ttttctccca    3900
tgaagacggt acgcgactgg gcgtggagca tctggtcgca ttgggtcacc agcaaatcgc    3960
gctgttagcg ggcccattaa gttctgtctc ggcgcgtctg cgtctggctg ctggcataa    4020 atatctcact cgcaatcaaa ttcagccgat agcggaacgg gaaggcgact ggagtgccat    4080
gtccggtttt caacaaacca tgcaaatgct gaatgagggc atcgttccca ctgcgatgct    4140
ggttgccaac gatcagatgg cgctgggcgc aatgcgcgcc attaccgagt ccgggctgcg    4200
cgttggtgcg gatatctcgg tagtgggata cgacgatacc gaagacagct catgttatat    4260
cccgccgtta accaccatca aacaggattt tcgcctgctg gggcaaacca gcgtggaccg    4320
cttgctgcaa ctctctcagg ccaggcggt gaagggcaat cagctgttgc ccgtctcact    4380
ggtgaaaaga aaaaccaccc tggcgcccaa tacgcaaacc gcctctcccc gcgcgttggc    4440
cgattcatta atgcagctgg cacgacaggt ttcccgactg gaaagcgggc agtgagcgca    4500
acgcaattaa tgtgagttag ctcactcatt aggcacccca ggctttacac tttatgcttc    4560
cggctcgtat gttgtgtgga attgtgagcg ataacaatt tcacacagga aacagctatg    4620
```

```
accatgatta cggattcact ggccgtcgtt ttacaacgtc gtgactggga aaaccctggc    4680
gttacccaac ttaatcgcct tgcagcacat ccccctttcg ccagctggcg taatagcgaa    4740
gaggcccgca ccgatcgccc ttcccaacag ttgcgcagcc tgaatggcga atggcgcttt    4800
gcctggtttc cggcaccaga agcggtgccg aaaagctggc tggagtgcga tcttcctgag    4860
gccgatactg tcgtcgtccc ctcaaactgg cagatgcacg gttacgatgc gcccatctac    4920
accaacgtaa cctatcccat tacggtcaat ccgccgtttg ttcccacgga gaatccgacg    4980
ggttgttact cgctcacatt taatgttgat gaaagctggc tacaggaagg ccagacgcga    5040 attattttg atggcgttgg aatt                                            5064
```

<210> SEQ ID NO 42
<211> LENGTH: 5918
<212> TYPE: DNA
<213> ORGANISM: Artificial sequence
<220> FEATURE:
<223> OTHER INFORMATION: Description of the artificial sequence:
      expression vector pET32a-dp-Pt(TME1)

<400> SEQUENCE: 42

```
atccggatat agttcctcct ttcagcaaaa aaccccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacggagct cgaattccta agcgtcaaca ccagcgaaca gcagcagaac aaccagaact    240
ttagcccagt taccaaccat agagaagtaa gcgataccag ccagaacacc ccagtgagca    300
ccagcgatcg ggtcggatcc acgcggaacc agaccaccac caccaccaga cagatccgat    360
tttggagatc cagaaccaga accggccagg ttagcgtcga ggaactcttt caactgacct    420
ttagacagtg cacccacttt ggttgccgcc acttcaccgt ttttgaacag cagcagagtc    480
gggataccac ggatgccata tttcggcgca gtgccagggt tttgatcgat gttcagtttt    540
gcaacggtca gtttgccctg atattcgtca gcgatttcat ccagaatcgg ggcgatcatt    600
ttgcacggac cgcaccactc tgcccagaaa tcgacgagga tcgccccgtc cgctttgagt    660
acatccgtgt caaaactgtc gtcagtcagg tgaataattt tatcgctcat atgtatatct    720
ccttcttaaa gttaaacaaa attatttcta gaggggaatt gttatccgct cacaattccc    780
ctatagtgag tcgtattaat ttcgcgggat cgagatcgat ctcgatcctc tacgccggac    840
gcatcgtggc cggcatcacc ggcgccacag gtgcggttgc tggcgcctat atcgccgaca    900
tcaccgatgg ggaagatcgg gctcgccact tcgggctcat gagcgcttgt ttcggcgtgg    960
gtatggtggc aggccccgtg gccgggggac tgttgggcgc catctccttg catgcaccat    1020
tccttgcggc ggcggtgctc aacggcctca acctactact gggctgcttc ctaatgcagg    1080
agtcgcataa gggagagcgt cgagatcccg gacaccatcg aatggcgcaa acctttcgc    1140 ggtatggcat gatagcgccc ggaagagagt caattcaggg tggtgaatgt gaaaccagta    1200
acgttatacg atgtcgcaga gtatgccggt gtctcttatc agaccgtttc ccgcgtggtg    1260
aaccaggcca gccacgtttc tgcgaaaacg cgggaaaaag tggaagcggc gatggcggag    1320
ctgaattaca ttcccaaccg cgtggcacaa caactggcgg gcaaacagtc gttgctgatt    1380
ggcgttgcca cctccagtct ggccctgcac gcgccgtcgc aaattgtcgc ggcgattaaa    1440
tctcgcgccg atcaactggg tgccagcgtg gtggtgtcga tggtagaacg aagcggcgtc    1500
gaagcctgta aagcggcggt gcacaatctt ctcgcgcaac gcgtcagtgg gctgatcatt    1560
```

```
aactatccgc tggatgacca ggatgccatt gctgtggaag ctgcctgcac taatgttccg   1620
gcgttatttc ttgatgtctc tgaccagaca cccatcaaca gtattatttt ctcccatgaa   1680
gacggtacgc gactgggcgt ggagcatctg gtcgcattgg gtcaccagca aatcgcgctg   1740
ttagcgggcc cattaagttc tgtctcggcg cgtctgcgtc tggctggctg gcataaatat   1800
ctcactcgca atcaaattca gccgatagcg aacgggaag gcgactggag tgccatgtcc    1860
ggttttcaac aaaccatgca aatgctgaat gagggcatcg ttcccactgc gatgctggtt   1920
gccaacgatc agatggcgct gggcgcaatg cgcgccatta ccgagtccgg gctgcgcgtt   1980
ggtgcggaca tctcggtagt gggatacgac gataccgaag acagctcatg ttatatcccg   2040
ccgttaacca ccatcaaaca ggattttcgc ctgctggggc aaaccagcgt ggaccgcttg   2100
ctgcaactct ctcagggcca ggcggtgaag ggcaatcagc tgttgcccgt ctcactggtg   2160
aaaagaaaaa ccaccctggc gcccaatacg caaaccgcct ctccccgcgc gttggccgat   2220
tcattaatgc agctggcacg acaggtttcc cgactggaaa gcgggcagtg agcgcaacgc   2280
aattaatgta agttagctca ctcattaggc accgggatct cgaccgatgc ccttgagagc   2340
cttcaaccca gtcagctcct ccggtgggc gcggggcatg actatcgtcg ccgcacttat    2400
gactgtcttc tttatcatgc aactcgtagg acaggtgccg gcagcgctct gggtcatttt   2460
cggcgaggac cgctttcgct ggagcgcgac gatgatcggc ctgtcgcttg cggtattcgg   2520
aatcttgcac gccctcgctc aagccttcgt cactggtccc gccaccaaac gtttcggcga   2580
gaagcaggcc attatcgccg gcatggcggc cccacgggtg cgcatgatcg tgctcctgtc   2640
gttgaggacc cggctaggct ggcggggttg ccttactggt tagcagaatg aatcaccgat   2700
acgcgagcga acgtgaagcg actgctgctg caaaacgtct gcgacctgag caacaacatg   2760
aatggtcttc ggtttccgtg tttcgtaaag tctggaaacg cggaagtcag cgccctgcac   2820
cattatgttc cggatctgca tcgcaggatg ctgctggcta ccctgtggaa cacctacatc   2880
tgtattaacg aagcgctggc attgaccctg agtgattttt ctctggtccc gccgcatcca   2940
taccgccagt tgtttaccct cacaacgttc cagtaaccgg gcatgttcat catcagtaac   3000
ccgtatcgtg agcatcctct ctcgtttcat cggtatcatt accccatga acagaaatcc   3060
cccttacacg gaggcatcag tgaccaaaca ggaaaaaacc gcccttaaca tggcccgctt   3120
tatcagaagc cagacattaa cgcttctgga gaaactcaac gagctggacg cggatgaaca   3180
ggcagacatc tgtgaatcgc ttcacgacca cgctgatgag cttaccgca gctgcctcgc    3240
gcgtttcggt gatgacggtg aaaacctctg acacatgcag ctcccggaga cggtcacagc   3300
ttgtctgtaa gcggatgccg ggagcagaca agcccgtcag ggcgcgtcag cgggtgttgg   3360
cgggtgtcgg ggcgcagcca tgacccagtc acgtagcgat agcggagtgt atactggctt   3420
aactatgcgg catcagagca gattgtactg agagtgcacc atatatgcgg tgtgaaatac   3480
cgcacagatg cgtaaggaga aaataccgca tcaggcgctc ttccgcttcc tcgctcactg   3540
actcgctgcg ctcggtcgtt cggctgcggc gagcggtatc agctcactca aaggcggtaa   3600
tacggttatc cacagaatca ggggataacg caggaaagaa catgtgagca aaaggccagc   3660
aaaaggccag gaaccgtaaa aaggccgcgt tgctggcgtt tttccatagg ctccgccccc   3720
ctgacgagca tcacaaaaat cgacgctcaa gtcagaggtg gcgaaacccg acaggactat   3780
aaagatacca ggcgtttccc cctggaagct ccctcgtgcg ctctcctgtt ccgaccctgc   3840
cgcttaccgg atacctgtcc gcctttctcc cttcgggaag cgtggcgctt tctcatagct   3900
```

```
cacgctgtag gtatctcagt tcggtgtagg tcgttcgctc caagctgggc tgtgtgcacg    3960
aaccccccgt tcagcccgac cgctgcgcct tatccggtaa ctatcgtctt gagtccaacc    4020
cggtaagaca cgacttatcg ccactggcag cagccactgg taacaggatt agcagagcga    4080
ggtatgtagg cggtgctaca gagttcttga agtggtggcc taactacggc tacactagaa    4140
ggacagtatt tggtatctgc gctctgctga agccagttac cttcggaaaa agagttggta    4200
gctcttgatc cggcaaacaa accaccgctg gtagcggtgg ttttttttgtt tgcaagcagc    4260 agattacgcg cagaaaaaaa ggatctcaag aagatccttt gatcttttct acggggtctg    4320
acgctcagtg gaacgaaaac tcacgttaag ggattttggt catgagatta tcaaaaagga    4380
tcttcaccta gatccttttta aattaaaaat gaagttttaa atcaatctaa agtatatatg    4440
agtaaacttg gtctgacagt taccaatgct taatcagtga ggcacctatc tcagcgatct    4500
gtctatttcg ttcatccata gttgcctgac tccccgtcgt gtagataact acgatacggg    4560
agggcttacc atctggcccc agtgctgcaa tgataccgcg agacccacgc tcaccggctc    4620
cagatttatc agcaataaac cagccagccg gaagggccga gcgcagaagt ggtcctgcaa    4680
ctttatccgc ctccatccag tctattaatt gttgccggga agctagagta agtagttcgc    4740
cagttaatag tttgcgcaac gttgttgcca ttgctgcagg catcgtggtg tcacgctcgt    4800
cgtttggtat ggcttcattc agctccggtt cccaacgatc aaggcgagtt acatgatccc    4860
ccatgttgtg caaaaaagcg gttagctcct tcggtcctcc gatcgttgtc agaagtaagt    4920
tggccgcagt gttatcactc atggttatgg cagcactgca taattctctt actgtcatgc    4980
catccgtaag atgcttttct gtgactggtg agtactcaac caagtcattc tgagaatagt    5040
gtatgcggcg accgagttgc tcttgcccgg cgtcaatacg ggataatacc gcgccacata    5100
gcagaacttt aaaagtgctc atcattggaa aacgttcttc ggggcgaaaa ctctcaagga    5160
tcttaccgct gttgagatcc agttcgatgt aacccactcg tgcacccaac tgatcttcag    5220
catcttttac tttcaccagc gtttctgggt gagcaaaaac aggaaggcaa aatgccgcaa    5280
aaaagggaat aagggcgaca cggaaatgtt gaatactcat actcttcctt tttcaatatt    5340
attgaagcat ttatcagggt tattgtctca tgagcggata catatttgaa tgtatttaga    5400
aaaataaaca ataggggtt ccgcgcacat ttccccgaaa agtgccacct gaaattgtaa    5460
acgttaatat tttgttaaaa ttcgcgttaa attttttgtta aatcagctca tttttttaacc    5520 aataggccga atcggcaaa atcccttata aatcaaaaga atagaccgag atagggttga    5580
gtgttgttcc agtttggaac aagagtccac tattaaagaa cgtggactcc aacgtcaaag    5640
ggcgaaaaac cgtctatcag ggcgatggcc cactacgtga accatcaccc taatcaagtt    5700
ttttggggtc gaggtgccgt aaagcactaa atcggaaccc taaagggagc ccccgattta    5760
gagcttgacg gggaaagccg gcgaacgtgg cgagaaagga agggaagaaa gcgaaaggag    5820
cgggcgctag ggcgctggca agtgtagcgg tcacgctgcg cgtaaccacc acacccgccg    5880
cgcttaatgc gccgctacag ggcgcgtccc attcgcca                            5918
```

<210> SEQ ID NO 43
<211> LENGTH: 5891
<212> TYPE: DNA
<213> ORGANISM: Artificial sequence
<220> FEATURE:
<223> OTHER INFORMATION: Description of the artificial sequence:
     expression vector pET32a-dp-Pt(TME2)

<400> SEQUENCE: 43

```
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacggagct cgaattccta agcttcagcc tgagagatca gcagcatcat ccacaggcaa     240
gagcaaacac gagcgtcagc cagcagcagg aacagcagaa caacgtattc cgggtcggat     300
ccacgcggaa ccagaccacc accaccacca gacagatcag atccagaacc agaaccggcc     360
aggttagcgt cgaggaactc tttcaactga cctttagaca gtgcacccac tttggttgcc     420
gccacttcac cgttttttgaa cagcagcaga gtcgggatac cacggatgcc atatttcggc     480
gcagtgccag ggttttgatc gatgttcagt tttgcaacgg tcagtttgcc ctgatattcg     540
tcagcgattt catccagaat cggggcgatc attttgcacg gaccgcacca ctctgcccag     600
aaatcgacga ggatcgcccc gtccgctttg agtacatccg tgtcaaaact gtcgtcagtc     660
aggtgaataa ttttatcgct catatgtata tctccttctt aaagttaaac aaaattattt     720
ctagaggga attgttatcc gctcacaatt cccctatagt gagtcgtatt aatttcgcgg     780
gatcgagatc gatctcgatc ctctacgccg gacgcatcgt ggccggcatc accggcgcca     840
caggtgcggt tgctggcgcc tatatcgccg acatcaccga tggggaagat cgggctcgcc     900
acttcgggct catgagcgct tgtttcggcg tgggtatggt ggcaggcccc gtggccgggg     960
gactgttggg cgccatctcc ttgcatgcac cattccttgc ggcggcggtg ctcaacggcc    1020
tcaacctact actgggctgc ttcctaatgc aggagtcgca taaggagag cgtcgagatc     1080
ccggacacca tcgaatggcg caaaaccttt cgcggtatgg catgatagcg cccggaagag    1140
agtcaattca gggtggtgaa tgtgaaacca gtaacgttat acgatgtcgc agagtatgcc    1200
ggtgtctctt atcagaccgt ttcccgcgtg gtgaaccagg ccagccacgt ttctgcgaaa    1260
acgcgggaaa aagtggaagc ggcgatggcg gagctgaatt acattcccaa ccgcgtggca    1320
caacaactgg cgggcaaaca gtcgttgctg attggcgttg ccacctccag tctggccctg    1380
cacgcgccgt cgcaaattgt cgcggcgatt aaatctcgcg ccgatcaact gggtgccagc    1440
gtggtggtgt cgatggtaga acgaagcggc gtcgaagcct gtaaagcggc ggtgcacaat    1500
cttctcgcgc aacgcgtcag tgggctgatc attaactatc cgctggatga ccaggatgcc    1560
attgctgtgg aagctgcctg cactaatgtt ccggcgttat ttcttgatgt ctctgaccag    1620
acacccatca acagtattat tttctcccat gaagacggta cgcgactggg cgtggagcat    1680
ctggtcgcat tgggtcacca gcaaatcgcg ctgttagcgg gcccattaag ttctgtctcg    1740
gcgcgtctgc gtctggctgg ctggcataaa tatctcactc gcaatcaaat tcagccgata    1800
gcggaacggg aaggcgactg gagtgccatg tccggttttc aacaaaccat gcaaatgctg    1860
aatgagggca tcgttcccac tgcgatgctg gttgccaacg atcagatggc gctgggcgca    1920
atgcgcgcca ttaccgagtc cgggctgcgc gttggtgcgg acatctcggt agtgggatac    1980
gacgataccg aagacagctc atgttatatc ccgccgttaa ccaccatcaa acaggatttt    2040
cgcctgctgg gcaaaccag cgtggaccgc ttgctgcaac tctctcaggg ccaggcggtg    2100
aagggcaatc agctgttgcc cgtctcactg gtgaaaagaa aaaccaccct ggcgcccaat    2160
acgcaaaccg cctctccccg cgcgttggcc gattcattaa tgcagctggc acgacaggtt    2220
tcccgactgg aaagcgggca gtgagcgcaa cgcaattaat gtaagttagc tcactcatta    2280
ggcacccggga tctcgaccga tgcccttgag agccttcaac ccagtcagct ccttccggtg    2340
ggcgcggggc atgactatcg tcgccgcact tatgactgtc ttctttatca tgcaactcgt    2400
```

```
aggacaggtg ccggcagcgc tctgggtcat tttcggcgag gaccgctttc gctggagcgc  2460
gacgatgatc ggcctgtcgc ttgcggtatt cggaatcttg cacgccctcg ctcaagcctt  2520
cgtcactggt cccgccacca aacgtttcgg cgagaagcag gccattatcg ccggcatggc  2580
ggccccacgg gtgcgcatga tcgtgctcct gtcgttgagg acccggctag gctggcgggg  2640
ttgccttact ggttagcaga atgaatcacc gatacgcgag cgaacgtgaa gcgactgctg  2700
ctgcaaaacg tctgcgacct gagcaacaac atgaatggtc ttcggtttcc gtgtttcgta  2760
aagtctggaa acgcggaagt cagcgccctg caccattatg ttccggatct gcatcgcagg  2820
atgctgctgg ctaccctgtg gaacacctac atctgtatta cgaagcgct  ggcattgacc  2880
ctgagtgatt tttctctggt cccgccgcat ccataccgcc agttgtttac cctcacaacg  2940
ttccagtaac cggcatgtt  catcatcagt aacccgtatc gtgagcatcc tctctcgttt  3000
catcggtatc attaccccca tgaacagaaa tcccccttac acggaggcat cagtgaccaa  3060
acaggaaaaa accgcccta  acatggcccg ctttatcaga agccagacat taacgcttct  3120
ggagaaactc aacgagctgg acgcggatga acaggcagac atctgtgaat cgcttcacga  3180
ccacgctgat gagctttacc gcagctgcct cgcgcgtttc ggtgatgacg gtgaaaacct  3240
ctgacacatg cagctcccgg agacggtcac agcttgtctg taagcggatg ccggagcag   3300
acaagcccgt cagggcgcgt cagcgggtgt tggcgggtgt cggggcgcag ccatgaccca  3360
gtcacgtagc gatagcggag tgtatactgg cttaactatg cggcatcaga gcagattgta  3420
ctgagagtgc accatatatg cggtgtgaaa taccgcacag atgcgtaagg agaaaatacc  3480
gcatcaggcg ctcttccgct tcctcgctca ctgactcgct gcgctcggtc gttcggctgc  3540
ggcgagcggt atcagctcac tcaaaggcgg taatacggtt atccacagaa tcagggata   3600
acgcaggaaa gaacatgtga gcaaaaggcc agcaaaaggc caggaaccgt aaaaaggccg  3660
cgttgctggc gtttttccat aggctccgcc cccctgacga gcatcacaaa aatcgacgct  3720
caagtcagag gtggcgaaac ccgacaggac tataaagata ccaggcgttt ccccctggaa  3780
gctccctcgt gcgctctcct gttccgaccc tgccgcttac cggatacctg tccgcctttc  3840
tcccttcggg aagcgtggcg ctttctcata gctcacgctg taggtatctc agttcggtgt  3900
aggtcgttcg ctccaagctg ggctgtgtgc acgaaccccc cgttcagccc gaccgctgcg  3960
ccttatccgg taactatcgt cttgagtcca acccggtaag cacgactta  tcgccactgg  4020
cagcagccac tggtaacagg attagcagag cgaggtatgt aggcggtgct acagagttct  4080
tgaagtggtg gcctaactac ggctacacta aaggacagt  atttggtatc tgcgctctgc  4140
tgaagccagt taccttcgga aaaagagttg gtagctcttg atccggcaaa caaaccaccg  4200
ctggtagcgg tggttttttt gtttgcaagc agcagattac gcgcagaaaa aaggatctc   4260
aagaagatcc tttgatcttt tctacggggt ctgacgctca gtggaacgaa aactcacgtt  4320
aagggatttt ggtcatgaga ttatcaaaaa ggatcttcac ctagatcctt ttaaattaaa  4380
aatgaagttt taaatcaatc taagtgtatat atgagtaaac ttggtctgac agttaccaat  4440
gcttaatcag tgaggcacct atctcagcga tctgtctatt tcgttcatcc atagttgcct  4500
gactccccgt cgtgtagata actacgatac gggagggctt accatctggc cccagtgctg  4560
caatgatacc gcgagaccca cgctcaccgg ctccagattt atcagcaata aaccagccag  4620
ccggaagggc cgagcgcaga agtggtcctg caactttatc cgcctccatc cagtctatta  4680
attgttgccg ggaagctaga gtaagtagtt cgccagttaa tagtttgcgc aacgttgttg  4740
```

-continued

```
ccattgctgc aggcatcgtg gtgtcacgct cgtcgtttgg tatggcttca ttcagctccg      4800
gttcccaacg atcaaggcga gttacatgat cccccatgtt gtgcaaaaaa gcggttagct      4860
ccttcggtcc tccgatcgtt gtcagaagta agttggccgc agtgttatca ctcatggtta      4920
tggcagcact gcataattct cttactgtca tgccatccgt aagatgcttt tctgtgactg      4980
gtgagtactc aaccaagtca ttctgagaat agtgtatgcg gcgaccgagt tgctcttgcc      5040
cggcgtcaat acgggataat accgcgccac atagcagaac tttaaaagtg ctcatcattg      5100
gaaaacgttc ttcggggcga aaactctcaa ggatcttacc gctgttgaga tccagttcga      5160
tgtaacccac tcgtgcaccc aactgatctt cagcatcttt tactttcacc agcgtttctg      5220
ggtgagcaaa aacaggaagg caaaatgccg caaaaaaggg aataagggcg acacggaaat      5280
gttgaatact catactcttc ctttttcaat attattgaag catttatcag ggttattgtc      5340
tcatgagcgg atacatattt gaatgtattt agaaaaataa acaataggg gttccgcgca      5400
catttccccg aaaagtgcca cctgaaattg taaacgttaa tattttgtta aaattcgcgt      5460
taaattttg ttaaatcagc tcatttttta accataggc gaaatcggc aaaatccctt      5520
ataaatcaaa agaatagacc gagataggt tgagtgttgt tccagtttgg aacaagagtc      5580
cactattaaa gaacgtggac tccaacgtca aagggcgaaa aaccgtctat cagggcgatg      5640
gcccactacg tgaaccatca ccctaatcaa gttttttggg gtcgaggtgc cgtaaagcac      5700
taaatcggaa ccctaaaggg agcccccgat ttagagcttg acggggaaag ccggcgaacg      5760
tggcgagaaa ggaagggaag aaagcgaaag gagcgggcgc tagggcgctg gcaagtgtag      5820
cggtcacgct gcgcgtaacc accacacccg ccgcgcttaa tgcgccgcta cagggcgcgt      5880
cccattcgcc a                                                            5891
```

<210> SEQ ID NO 44
<211> LENGTH: 2617
<212> TYPE: DNA
<213> ORGANISM: Artificial sequence
<220> FEATURE:
<223> OTHER INFORMATION: Description of the artificial sequence:
      expression vector pT7-7-dp-Pt(TME1)

<400> SEQUENCE: 44

```
aattctcatg tttgacagct tatcatcgat gataagcttg gctgcaggt cgactctaga       60
ggatccccgg gcgcgaattc ctaagcgtca acaccagcga acagcagcag aacaaccaga      120
actttagccc agttaccaac catagagaag taagcgatac cagccagaac accccagtga      180
gcaccagcga tcgggtccat atgtatatct ccttcttaaa gttaaacaaa attatttcta      240
gagggaaacc gttgtggtct ccctatagtg agtcgtatta atttcgaagt ctatcagaag      300
ttcgaatcgc tgggcctcgc gcgtttcggt gatgacggtg aaaacctctg acacatgcag      360
ctcccggaga cggtcacagc ttgtctgtaa gcggatgccg ggagcagaca agcccgtcag      420
ggcgcgtcag cgggtgttgg cgggtgtcgg ggcgcagcca tgacccagtc acgtagcgat      480
agcggagtgt atatactggc ttaactatgc ggcatcagag cagattgtac tgagagtgca      540
ccataggaag atcttccgga agatcttcct atgcggtgtg aaataccgca cagatgcgta      600
aggagaaaat accgcatcag cgctcttccc gcttcctcgc tcactgactc gctgcgctcg      660
gtcgttcggc tgcggcgagc ggtatcagct cactcaaagg cggtaatacg gttatccaca      720
gaatcagggg ataacgcagg aaagaacatg tgagcaaaag gccagcaaaa ggccaggaac      780
cgtaaaaagg ccgcgttgct ggcgtttttc cataggctcc gccccctga cgagcatcac      840
```

```
aaaaatcgac gctcaagtca gaggtggcga aacccgacag gactataaag ataccaggcg    900
tttcccctg  gaagctccct cgtgcgctct cctgttccga ccctgccgct taccggatac    960
ctgtccgcct ttctcccttc gggaagcgtg gcgctttctc aatgctcacg ctgtaggtat   1020
ctcagttcgg tgtaggtcgt tcgctccaag ctgggctgtg tgcacgaacc ccccgttcag   1080
cccgaccgct gcgccttatc cggtaactat cgtcttgagt ccaacccggt aagacacgac   1140
ttatcgccac tggcagcagc cactggtaac aggattagca gagcgaggta tgtaggcggt   1200
gctacagagt tcttgaagtg gtggcctaac tacggctaca ctagaaggac agtatttggt   1260
atctgcgctc tgctgaagcc agttaccttc ggaaaaagag ttggtagctc ttgatccggc   1320
aaacaaacca ccgctggtag cggtggtttt tttgtttgca agcagcagat tacgcgcaga   1380
aaaaaaggat ctcaagaaga tcctttgatc ttttctacgg ggtctgacgc tcagtggaac   1440
gaaaactcac gttaagggat tttggtcatg agattatcaa aaggatcttc acctagatc    1500
cttttaattc ttgaagacga agggcctcg  tgatacgcct atttttatag gttaatgtca   1560
tgataataat ggtttcttag acgtcaggtg gcacttttcg gggaaatgtg cgcggaaccc   1620
ctatttgttt attttttctaa atacattcaa atatgtatcc gctcatgaga caataaccct   1680
gataaatgct tcaataatat tgaaaaagga gagtatgag  tattcaacat ttccgtgtcg   1740
cccttattcc cttttttgcg gcattttgcc ttcctgtttt tgctcaccca gaaacgctgg   1800
tgaaagtaaa agatgctgaa gatcagttgg gtgcacgagt gggttacatc gaactggatc   1860
tcaacagcgg taagatcctt gagagttttc gccccgaaga acgttttcca atgatgagca   1920
cttttaaagt tctgctatgt ggcgcggtat tatcccgtgt tgacgccggg caagagcaac   1980
tcggtcgccg catacactat tctcagaatg acttggttga gtactcacca gtcacagaaa   2040
agcatcttac ggatggcatg acagtaagag aattatgcag tgctgccata accatgagtg   2100
ataacactgc ggccaactta cttctgacaa cgatcggagg accgaaggag ctaaccgctt   2160
ttttgcacaa catgggggat catgtaactc gccttgatcg ttgggaaccg gagctgaatg   2220
aagccatacc aaacgacgag cgtgacacca cgatgcctgt agcaatggca acaacgttgc   2280
gcaaactatt aactggcgaa ctacttactc tagcttcccg gcaacaatta atagactgga   2340
tggaggcgga taaagttgca ggaccacttc tgcgctcggc ccttccggct ggctggttta   2400
ttgctgataa atctggagcc ggtgagcgtg ggtctcgcgg tatcattgca gcactggggc   2460
cagatggtaa gccctcccgt atcgtagtta tctacacgac ggggagtcag gcaactatgg   2520
atgaacgaaa tagacagatc gctgagatag gtgcctcact gattaagcat tggtaactgt   2580
cagaccaagt ttactcatat atactttaga ttgattt                            2617
```

<210> SEQ ID NO 45
<211> LENGTH: 2599
<212> TYPE: DNA
<213> ORGANISM: Artificial sequence
<220> FEATURE:
<223> OTHER INFORMATION: Description of the artificial sequence:
      expression vector pT7-7-dp-Pt(TME2)

<400> SEQUENCE: 45

```
aattctcatg tttgacagct tatcatcgat gataagcttg gctgcaggt  cgactctaga     60
ggatccccgg gcgcgaattc ctaagcttca gcctgagaga tcagcagcat catccacagg    120
caagagcaaa cacgagcgtc agccagcagc aggaacagca gaacaacgta ttccgggtcc    180
atatgtatat ctccttctta aagttaaaca aaattatttc tagagggaaa ccgttgtggt    240
```

```
ctccctatag tgagtcgtat taatttcgaa gtctatcaga agttcgaatc gctgggcctc    300
gcgcgtttcg gtgatgacgg tgaaaacctc tgacacatgc agctcccgga gacggtcaca    360
gcttgtctgt aagcggatgc cgggagcaga caagcccgtc agggcgcgtc agcgggtgtt    420
ggcgggtgtc ggggcgcagc catgacccag tcacgtagcg atagcggagt gtatatactg    480
gcttaactat gcggcatcag agcagattgt actgagagtg caccatagga agatcttccg    540
gaagatcttc ctatgcggtg tgaaataccg cacagatgcg taaggagaaa ataccgcatc    600
aggcgctctt ccgcttcctc gctcactgac tcgctgcgct cggtcgttcg gctgcggcga    660
gcggtatcag ctcactcaaa ggcggtaata cggttatcca cagaatcagg ggataacgca    720
ggaaagaaca tgtgagcaaa aggccagcaa aaggccagga accgtaaaaa ggccgcgttg    780
ctggcgtttt tccataggct ccgcccccct gacgagcatc acaaaaatcg acgctcaagt    840
cagaggtggc gaaacccgac aggactataa agataccagg cgtttccccc tggaagctcc    900
ctcgtgcgct ctcctgttcc gaccctgccg cttaccggat acctgtccgc ctttctccct    960
tcgggaagcg tggcgctttc tcaatgctca cgctgtaggt atctcagttc ggtgtaggtc   1020
gttcgctcca agctgggctg tgtgcacgaa ccccccgttc agcccgaccg ctgcgcctta   1080
tccggtaact atcgtcttga gtccaacccg gtaagacacg acttatcgcc actggcagca   1140
gccactggta acaggattag cagagcgagg tatgtaggcg gtgctacaga gttcttgaag   1200
tggtggccta actacggcta cactagaagg acagtatttg gtatctgcgc tctgctgaag   1260
ccagttacct tcggaaaaag agttggtagc tcttgatccg gcaaacaaac caccgctggt   1320
agcggtggtt ttttgtttg caagcagcag attacgcgca gaaaaaaagg atctcaagaa   1380
gatcctttga tcttttctac ggggtctgac gctcagtgga acgaaaactc acgttaaggg   1440
attttggtca tgagattatc aaaaaggatc ttcacctaga tccttttaat tcttgaagac   1500
gaaagggcct cgtgatacgc ctatttttat aggttaatgt catgataata atggtttctt   1560
agacgtcagg tggcactttt cggggaaatg tgcgcggaac ccctatttgt ttatttttct   1620
aaatacattc aaatatgtat ccgctcatga caataaccct gataaatgc ttcaataat   1680
attgaaaaag gaagagtatg agtattcaac atttccgtgt cgcccttatt cccttttttg   1740
cggcattttg ccttcctgtt tttgctcacc cagaaacgct ggtgaaagta aaagatgctg   1800
aagatcagtt gggtgcacga gtgggttaca tcgaactgga tctcaacagc ggtaagatcc   1860
ttgagagttt cgccccgaa gaacgttttc caatgatgag cacttttaaa gttctgctat   1920
gtggcgcggt attatcccgt gttgacgccg ggcaagagca actcggtcgc cgcatacact   1980
attctcagaa tgacttggtt gagtactcac cagtcacaga aaagcatctt acggatggca   2040
tgacagtaag agaattatgc agtgctgcca taaccatgag tgataacact gcggccaact   2100
tacttctgac aacgatcgga ggaccgaagg agctaaccgc ttttttgcac aacatggggg   2160
atcatgtaac tcgccttgat cgttgggaac cggagctgaa tgaagccata ccaaacgacg   2220
agcgtgacac cacgatgcct gtagcaatgg caacaacgtt gcgcaaacta ttaactggcg   2280
aactacttac tctagcttcc cggcaacaat taatagactg gatggaggcg gataaagttg   2340
caggaccact tctgcgctcg gcccttccgg ctggctggtt tattgctgat aaatctggag   2400
ccggtgagcg tgggtctcgc ggtatcattg cagcactggg gccagatggt aagccctccc   2460
gtatcgtagt tatctacacg acggggagtc aggcaactat ggatgaacga atagacaga   2520
tcgctgagat aggtgcctca ctgattaagc attggtaact gtcagaccaa gtttactcat   2580
atatacttta gattgattt                                                2599
```

<210> SEQ ID NO 46
<211> LENGTH: 271
<212> TYPE: PRT
<213> ORGANISM: Artificial sequence
<220> FEATURE:
<223> OTHER INFORMATION: Description of the artificial sequence: fusion protein GST-DP-TME1

<400> SEQUENCE: 46

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Ser Gly Gly
    210                 215                 220

Gly Gly Gly Leu Val Pro Arg Gly Ser Asp Pro Ile Ala Gly Ala His
225                 230                 235                 240

Trp Gly Val Leu Ala Gly Ile Ala Tyr Phe Ser Met Val Gly Asn Trp
                245                 250                 255

Ala Lys Val Leu Val Val Leu Leu Leu Phe Ala Gly Val Asp Ala
            260                 265                 270
```

<210> SEQ ID NO 47
<211> LENGTH: 265
<212> TYPE: PRT
<213> ORGANISM: Artificial sequence
<220> FEATURE:
<223> OTHER INFORMATION: Description of the artificial sequence: fusion protein GST-DP-TME2

<400> SEQUENCE: 47

```
Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30
```

-continued

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ser Gly Gly
    210                 215                 220

Gly Gly Gly Leu Val Pro Arg Gly Ser Asp Pro Glu Tyr Val Val Leu
225                 230                 235                 240

Leu Phe Leu Leu Leu Ala Asp Ala Arg Val Cys Ser Cys Leu Trp Met
                245                 250                 255

Met Leu Leu Ile Ser Gln Ala Glu Ala
        260                 265

<210> SEQ ID NO 48
<211> LENGTH: 170
<212> TYPE: PRT
<213> ORGANISM: Artificial sequence
<220> FEATURE:
<223> OTHER INFORMATION: Description of the artificial sequence:
      fusion protein TrX-DP-TME1

<400> SEQUENCE: 48

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly Ser Pro Lys Ser Asp Leu Ser Gly Gly Gly Gly Gly Leu Val

```
              115                 120                 125

Pro Arg Gly Ser Asp Pro Ile Ala Gly Ala His Trp Gly Val Leu Ala
        130                 135                 140

Gly Ile Ala Tyr Phe Ser Met Val Gly Asn Trp Ala Lys Val Leu Val
145                 150                 155                 160

Val Leu Leu Leu Phe Ala Gly Val Asp Ala
                165                 170

<210> SEQ ID NO 49
<211> LENGTH: 161
<212> TYPE: PRT
<213> ORGANISM: Artificial sequence
<220> FEATURE:
<223> OTHER INFORMATION: Description of the artificial sequence:
      fusion protein TrX-DP-TME2

<400> SEQUENCE: 49

Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
                 20                  25                  30

Cys Gly Pro Cys Lys Met Ile Ala Pro Ile Leu Asp Glu Ile Ala Asp
             35                  40                  45

Glu Tyr Gln Gly Lys Leu Thr Val Ala Lys Leu Asn Ile Asp Gln Asn
         50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly Ser Asp Leu Ser Gly Gly Gly Gly Leu Val Pro Arg Gly
            115                 120                 125

Ser Asp Pro Glu Tyr Val Val Leu Leu Phe Leu Leu Leu Ala Asp Ala
        130                 135                 140

Arg Val Cys Ser Cys Leu Trp Met Met Leu Leu Ile Ser Gln Ala Glu
145                 150                 155                 160

Ala

<210> SEQ ID NO 50
<211> LENGTH: 39
<212> TYPE: PRT
<213> ORGANISM: Artificial sequence
<220> FEATURE:
<223> OTHER INFORMATION: Description of the artificial sequence:
      fusion protein M-DP-TME1

<400> SEQUENCE: 50

Met Asp Pro Ile Ala Gly Ala His Trp Gly Val Leu Ala Gly Ile Ala
  1               5                  10                  15

Tyr Phe Ser Met Val Gly Asn Trp Ala Lys Val Leu Val Val Leu Leu
                 20                  25                  30

Leu Phe Ala Gly Val Asp Ala
             35

<210> SEQ ID NO 51
<211> LENGTH: 33
<212> TYPE: PRT
<213> ORGANISM: Artificial sequence
```

```
<220> FEATURE:
<223> OTHER INFORMATION: Description of the artificial sequence:
      fusion protein M-DP-TME2

<400> SEQUENCE: 51

Met Asp Pro Glu Tyr Val Val Leu Leu Phe Leu Leu Leu Ala Asp Ala
 1               5                  10                  15

Arg Val Cys Ser Cys Leu Trp Met Met Leu Leu Ile Ser Gln Ala Glu
            20                  25                  30

Ala

SEQ ID NO 52

<211> LENGTH: 239
<212> TYPE: PRT
<213> ORGANISM: Artificial sequence
<220> FEATURE:
<223> OTHER INFORMATION: Description of the artificial sequence:
      glutathion transferase (GST)

<400> SEQUENCE: 52

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ser Gly Gly
    210                 215                 220

Gly Gly Gly Leu Val Pro Arg Gly Ser Pro Gly Ile His Arg Asp
225                 230                 235

<210> SEQ ID NO 53
<211> LENGTH: 170
<212> TYPE: PRT
<213> ORGANISM: Artificial sequence
<220> FEATURE:
<223> OTHER INFORMATION: Description of the artificial sequence:
      thioredoxine (TrX)
```

```
<400> SEQUENCE: 53

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly Ser Pro Lys Ser Asp Leu Ser Gly Gly Gly Gly Leu Val
            115                 120                 125

Pro Arg Gly Ser Asp Pro Ile Ala Gly Ala His Trp Gly Val Leu Ala
        130                 135                 140

Gly Ile Ala Tyr Phe Ser Met Val Gly Asn Trp Ala Lys Val Leu Val
145                 150                 155                 160

Val Leu Leu Leu Phe Ala Gly Val Asp Ala
                165                 170
```

SYSTEMS FOR EXPRESSING TOXIC PROTEINS, VECTORS AND METHOD OF PRODUCING TOXIC PROTEINS

FIELD OF THE INVENTION

The present invention relates to systems for expressing toxic proteins, to expression vectors comprising one of these systems, to prokaryotic cells transformed with these systems, and also to a method for synthesizing a toxic protein using these expression systems.

It enables, for example, the overproduction in a prokaryotic cell, for example *Escherichia coli* (*E. coli*), of toxic hydrophobic proteins or peptides, for example the overproduction of transmembrane domains of viral envelope proteins.

It finds many applications in particular in research concerning the mechanisms of viral infections, and in the search for and development of novel active principles for combating viral infections.

In the description which follows, the references between square brackets [ ] refer to the attached reference list.

BACKGROUND OF THE INVENTION

Determination of the three-dimensional (3D) structure is a decisive step in the structural and functional understanding of proteins.

Very great efforts and means have been, and are being, used to achieve this aim, and have been amplified with the accumulation of data provided by the genome sequencing programmes [1].

The two main techniques for establishing these protein structures are X-ray diffraction, carried out using crystallized proteins, and nuclear magnetic resonance (NMR) carried out using proteins in solution. NMR, which is very suitable for studying proteins with a molecular mass of less than 20 kDa, requires however, like X-ray diffraction, the production of large amounts of material. It also means, in most cases, that material enriched in $^{15}$N and/or $^{13}$C must be prepared.

In this context, the bacterium is a means of production that is widely used by the scientific community [2]. The overexpression of proteins in bacteria does not, however, occur without problems. In fact, it gives rise to three situations:

The first case, which is ideal, is that where the protein is overproduced in a form that is correctly spatially folded during its synthesis in vivo. This is not a rare situation, but neither is it frequent. It concerns essentially soluble proteins that are small, i.e. approximately 20 to 50 kDa.

The second case, the most common, is that where the protein is overproduced and aggregated in the form of inclusion bodies. This concerns polytopic and/or large proteins. In this case, the kinetics of folding of the protein are clearly slower than its rate of biosynthesis. This promotes exposure of the hydrophobic regions of the protein, that are normally buried in the core thereof, to the aqueous solvent and generates non-specific interactions that result in the formation of insoluble aggregates. According to the degree of disorder of this folding, the inclusion bodies can be solubilized/unfolded under nonnative conditions, with urea or guanidine. The solubilized protein is then subjected to various treatments, such as dialysis or dilution, so as to promote, successfully in certain cases, a native 3D folding.

The third case is that where the expression engenders a varying degree of toxicity. This goes from an absence of expression product if the bacterium manages to adapt itself, to death of the bacterium if the product is too toxic. It is a case which occurs quite frequently and most commonly with membrane proteins or membrane protein domains, for instance those of the envelope proteins of the hepatitis C virus [5] or of the human immunodeficiency virus [6].

The problem of toxicity relates essentially to the expression of membrane proteins, i.e. proteins having a hydrophobic domain. Now, these proteins are of growing interest. Firstly, they are relatively numerous since the establishment of the various genomes confirms that they represent approximately 30% of the proteins potentially encoded by these genomes [7]. Secondly, they constitute 70% of the therapeutic targets and their alteration is the cause of many genetic diseases [8].

It is therefore essential to develop methods that facilitate or allow the expression of such proteins or of their membrane portion.

Efforts have been made in this respect with, for example, the development of bacterial strains that either show better tolerance to the expression of membrane proteins [9, 10], or have a stricter regulation of the mechanism in the expression, as in the case of the *E. coli* strain BL21(DE3)pLysS developed by Stratagene. However, these improvements do not make it possible to eliminate the toxicity phenomenon in all cases, in particular in the expression of hydrophobic peptides corresponding to membrane anchors.

The treatment of hepatitis C currently represents one of the major high-stakes areas of medicine. Hepatitis C is caused by the hepatitis C virus (HCV) of the family of flaviviridae and which specifically infects hepatic cells [11]. This virus consists of a positive RNA of approximately 9500 bases which encodes a polyprotein of 3033 residues [13], symbolized in the attached FIG. 1 by the rectangle 1A. This polyprotein is cleaved, after expression, by endogenous and exogenous proteases, so as to give rise to 10 different proteins. Two of them, called E1 and E2, are glycosylated and form the envelope of the virus. They each have membrane domains called TM, in particular TME1 for the E1 protein and TME2 for the E2 protein. The cleavage positions that generate them are indicated in FIG. 1 by arrows with, mentioned below, a number which corresponds to the position in the polyprotein of the first amino acid of sequence resulting from the cleavage. The E1 and E2 proteins are symbolized by a rectangle. The white portion of each rectangle corresponds to the ectodomain (ed) and the shaded domain to the transmembrane region (TM). The primary sequence of the TMs is indicated at the bottom of the figure in one-letter-code, with numbers corresponding to the position of the amino acids in the polyprotein located at the ends of these domains. The stars indicate the hydrophobic amino acids. These membrane domains or membrane regions of the virus have particular association properties that condition the structuring of the viral envelope [12]. In this respect, they constitute potential therapeutic targets. An understanding of the mechanism of association of the virus requires studies of the 3D structure of these domains, in particular by means of the abovementioned techniques, which involves producing these peptides in abundant amounts, and also preferably via the biosynthetic pathway in order to allow $^{15}$N and/or $^{13}$C isotope labelling.

The various E1 expression trials of the prior art, in particular in *E. coli* [14][5] or in sf9 insect cells infected with baculoviruses [15], have not made it possible to overproduce this E1 protein, in particular due to the toxicity induced by its expression, including in the "resistant" *E. coli* BL21(DE3) pLysS strains described above. There has been no E2 protein overexpression trial in bacteria. These toxicity problems are essentially due to the C-terminal region of the two proteins, that is rich in hydrophobic amino acids which form transmembrane domains that provide the anchoring to the membrane of the endoplasmic reticulum.

There is therefore a real need for a system for expressing toxic proteins which does not have the drawbacks, and limitations, deficiencies and disadvantages of the techniques of the prior art.

In addition, there is a real need for an expression vector comprising such a system for expressing toxic proteins, making it possible to carry out a method for producing toxic proteins which does not have the drawbacks, limitations, deficiencies and disadvantages of the techniques of the prior art.

SUMMARY OF THE INVENTION

The aim of the present invention is precisely to provide a system for expressing a toxic protein, which satisfies, inter alia, the needs indicated above.

This aim, and others, are achieved, in accordance with the invention, by means of an expression system characterized in that it comprises successively, in the 5'-3' direction, a nucleotide sequence encoding the dipeptide Asp-Pro, referred to below as dp sequence, and a nucleotide sequence (pt) encoding a toxic protein (Pt). This system will be identified below by: dp-pt.

DETAILED DESCRIPTION OF THE INVENTION

According to a particularly preferred embodiment of the present invention, the expression system also comprises, upstream of the dp sequence, a nucleotide sequence (ps) encoding a soluble protein (Ps). This soluble protein may be, for example, glutathione S-transferase (GST) or thioredoxin (TrX) or another equivalent soluble protein. This expression system according to the invention will be identified below by: ps-dp-pt.

The dp-pt expression system of the present invention, which comprises a sequence encoding Asp-Pro (DP in one-letter code) placed upstream of the nucleotide sequence of the toxic protein, makes it possible, entirely unexpectedly, to suppress the toxic effect of the protein for the host cell. In addition, the inventors have noted that, entirely surprisingly, the suppression of toxicity of the protein in the host is even more effective with the ps-dp-pt expression system when the toxic peptide is produced as a C-terminal fusion with a soluble protein, for example glutathione S-transferase or thioredoxin, with the sequence Asp-Pro inserted between the soluble protein and the toxic peptide.

The dp-pt or ps-dp-pt expression system of the present invention makes it possible to overproduce toxic proteins in host cells, in particular hydrophobic proteins, especially peptides which correspond to, or which comprise, hydrophobic domains of membrane-anchored proteins which may involve, for example, a membrane protein or a domain of a membrane protein. It may involve, for example, a protein of a virus, for example of a hepatitis C virus, of an AIDS virus, or of any other virus that is pathogenic for humans and, in general, for mammals.

For example, the dp-pt or ps-dp-pt system of the invention makes it possible to overproduce, in a host such as E. coli, the transmembrane domains of the E1 and E2 proteins of the hepatitis C virus, called TME1 and TME2, corresponding respectively to the sequences:

```
TME1:
                                            SEQ ID NO: 1
347-MIAGAHWGVLAGIAYFSMVGNWAKVLVVLLLFAGVDA-383

TME2:
                                            SEQ ID NO: 2
717-MEYVVLLFLLLADARVCSCLWMMLLISQAEA-746
``` whereas this was not possible with the techniques of the prior art.

The nucleotide sequences that can be used for constituting the dp-pt system of the invention encoding the TME1 (dp-pt$_{(TME1)}$) or TME2 (dp-pt$_{(TME2)}$) proteins can be any of the possible sequences encoding respectively the DP-TME1 and DP-TME2 fusion proteins. The sequences encoding the TME1 and TME2 proteins may advantageously be, for example, SEQ ID NO: 3 and SEQ ID NO: 4, respectively, of the attached sequence listing. To obtain the dp-pt system, the dp sequence encoding the dipeptide Asp-Pro (DP) is added to these sequences.

The nucleotide sequences that can be used for constituting the ps-dp-pt system of the invention encoding the TME1 (ps-dp-pt$_{(TME1)}$) or TME2 (ps-dp-pt$_{(TME2)}$) proteins may be any of the possible sequences encoding the Ps-DP-TME1 and Ps-DP-TME2 fusion proteins, respectively. They may advantageously be, for example, the sequences ID No. 34, ID No. 35 and ID No. 36 of the attached sequence listing for TME1, making it possible to obtain a Ps-DP-TME1 chimeric protein. They may advantageously be, for example, the sequences ID No. 37, ID No. 38 and ID No. 39 of the attached sequence listing for TME2, making it possible to obtain a Ps-DP-TME2 chimeric protein.

In fact, the abovementioned nucleotide sequences have optimized codons for the expression of TME1 and TME2 in a bacterium, for example in E. coli.

A large number of HCV RNA sequences producing an infectious phenotype exist: these sequences can also be used in the present invention.

The sequence encoding the dipeptide Asp-Pro may be, for example: gacccg, or any other sequence encoding this dipeptide.

The sequence encoding GST may be, for example, that present in the pGEXKT plasmids, the sequence of which corresponds to SEQ ID NO: 29 of the attached sequence listing, or any equivalent sequence, i.e. encoding this soluble protein. The sequence encoding TrX may be, for example, that present in the pET32a+ expression plasmid, the sequence of which corresponds to SEQ ID NO: 30 of the attached sequence listing, or any equivalent sequence, i.e. encoding this soluble protein.

For the production of the toxic protein, the dp-pt or ps-dp-pt expression system of the invention is placed inside a host cell, for example by cloning in an appropriate plasmid, by means of the usual techniques for transforming a host in genetic recombination techniques.

The plasmid into which the expression system of the present invention may be cloned so as to form this vector will be chosen in particular according to the host cell. It may be, for example, the pT7-7 plasmid (SEQ TD NO: 33 of the attached sequence listing), a plasmid of the pGEX series (for example of SEQ ID NO: 31 of the attached sequence listing), sold for example by the company Pharmacia, or a plasmid of the pET32 series (for example of sequence ID No: 32 of the attached sequence listing), sold for example by the company Novagen.

The plasmids of the pGEX series and of the pET32 series will advantageously be used for implementing the present invention. In fact, they already comprise a ps sequence encoding a soluble protein (Ps), respectively glutathione S-transferase and thioredoxin. Thus, advantageously, the dp-pt system will be cloned into these plasmids downstream of this ps sequence encoding the soluble protein.

The present invention therefore also relates to an expression vector comprising a dp-pt or ps-dp-pt expression system according to the invention; in particular, a vector comprising a dp-pt expression system according to the invention and the oligonucleotide sequence of the pT7-7 plasmid, or a vector comprising a ps-dp-pt expression system according to the invention and the oligonucleotide sequence of a pGEX plasmid or of a pET32 plasmid.

For example, the expression vectors of the present invention that are suitable for a bacterial host such as *E. coli* and that allow overexpression of the abovementioned TME1 membrane protein may advantageously have an oligonucleotide sequence chosen from the sequences ID No. 40 (with pGEXKT), ID No. 42 (with pET32a+) and ID No. 44 (with PT7-7) of the attached sequence listing.

For example, the expression vectors of the present invention that are suitable for a bacterial host such as *E. coli* and that allow overexpression of the abovementioned TME2 membrane protein may advantageously have an oligonucleotide sequence chosen from the sequences ID No. 41 (with pGEXKT), ID No. 43 (with pET32a+) and ID No. 45 (with pT7-7) of the attached sequence listing.

In fact, the abovementioned expression vectors have codons that are optimized for the expression of the chimeric proteins of the present invention, including TME1 and TME2, in a bacterium, for example in *E. coli*.

The present invention also relates to a prokaryotic cell transformed with an expression vector according to the invention. This prokaryotic cell transformed with the expression vector of the present invention should preferably allow overexpression of the toxic protein for which the vector codes. Thus, any host cell capable of expressing the expression vector of the present invention can be used, for example *E. coli*, advantageously the *E. coli* strain BL21(DE3)pLysS.

The present invention also relates to a method for producing a toxic protein by genetic recombination, comprising the following steps:
- transforming a host cell with an expression vector according to the invention,
- culturing the transformed host cell under culture conditions such that it produces a fusion protein comprising the dipeptide Asp-Pro followed by the peptide sequence of the toxic protein from said expression vector, and isolating said fusion protein, and
- cleaving said fusion protein so as to recover the toxic protein.

The steps for transforming, culturing and isolating the chimeric protein produced can be carried out by means of the usual techniques of genetic recombination, for example by means of techniques such as those that are described in document [25].

The step consisting in isolating the fusion protein can be carried out by means of the usual techniques known to those skilled in the art for isolating a protein from a cell extract.

The fusion protein produced by means of the method of the invention has a "soluble protein-Asp-Pro-toxic protein" sequence. In the present description, the dipeptide Asp-Pro is also called DP according to the one-letter amino acid code.

For example, when the toxic protein is TME1, the fusion protein may have the SEQ ID NO: 46 of the attached sequence listing, which corresponds to the GST-DP-TME1 fusion protein; the SEQ ID NO: 48 of the attached sequence listing, which corresponds to the TrX-DP-TME1 fusion protein; or the SEQ ID NO: 50 of the attached sequence listing, which corresponds to the M-DP-TME1 fusion protein of the attached sequence listing.

For example, when the toxic protein is TME2, the fusion protein may have the SEQ ID NO: 47 of the attached sequence listing, which corresponds to the GST-DP-TME2 fusion protein; the SEQ ID NO: 49 of the attached sequence listing, which corresponds to the TrX-DP-TME2 fusion protein; or the SEQ ID NO: 51 of the attached sequence listing, which corresponds to the M-DP-TME2 fusion protein of the attached sequence listing.

The step consisting of cleavage of this fusion protein can advantageously be carried out by means of formic acid, which cleaves the fusion protein at the dipeptide Asp-Pro. It may be carried out, moreover, by means of any appropriate technique known to those skilled in the art for recovering a protein from a sample using a fusion protein.

The inventors are the first to have found a system that is really effective for producing and even overproducing, in particular in the *Escherichia coli* (*E. coli*) bacterium, hydrophobic peptides corresponding to the membrane domains of the E1 and E2 proteins of the hepatitis C virus envelope, the expression of which is lethal for the microorganism.

The field of application of the present invention concerns mainly the production of hydrophobic peptides on a large scale, in particular for fundamental and industrial research. In addition, the production of the chimeric protein consisting of the soluble protein, of the dipeptide Asp-Pro and of the hyrophohic peptide can be used for a functional purpose, in particular for obtaining information on the degree of oligomerization of the membrane domain or else on its heteropolymerization capacity.

The fusion proteins, or chimeric proteins, are produced via their coding DNA present, for example, in commercial plasmids and following which is introduced, in phase, the DNA encoding the Asp-Pro sequence followed by that encoding the toxic peptide. This application can be commercialized in the form of bacterial expression plasmids which will include the sequence of the Asp Pro site, downstream of that of the soluble proteins already present. The corresponding plasmid will be described, for example, as a tool that facilitates the production, via the biological pathway, of toxic membrane peptides or proteins.

Thus, the present invention is applicable to any system for overexpressing recombinant proteins, with or without fusion to a soluble protein such as, for example, GST or thioredoxin, including a non-natural Asp-Pro sequence inserted upstream of a sequence encoding a toxic domain of the protein, for example a membrane domain of a protein.

Other characteristics and advantages of the present invention will become further apparent to those skilled in the art on reading the following examples given by way of non limiting illustration, with reference to the sequence listing and to the figures that are attached.

BRIEF DESCRIPTION OF THE ATTACHED SEQUENCE LISTING

SEQ ID NOS: 1 and 2: peptide sequences of TME1 and of TME2, respectively.
SEQ ID NOS: 3 and 4: sequences encoding the TME1 peptide and the TME2 peptide, respectively.

SEQ ID NOS: 5 and 6: respectively, oligonucleotide (+) for insertion into pT7-7 (OL13(+)) and oligonucleotide (−) for insertion into pT7-7 (OL14(−)).

SEQ ID NOS: 7 and 8: respectively, coding sense DNA of TME1+cla I site in the 3' position and anticoding sense DNA of TME1+cla I site in the 5' position (sequence complementary to the SEQ ID NO: 7).

SEQ ID NOS: 9 and 10: respectively, coding sense oligonucleotide (OL11(+)) and anticoding sense oligonucleotide (OL12(−)) for the synthesis of TME1.

SEQ ID NO: 11: oligonucleotide (+) for insertion into pGEXKT without dp site (OL15(+)).

SEQ ID NO: 12: oligonucleotide (+) for insertion into pGEXKT with dp site (OL17(+)).

SEQ ID NO: 13: oligonucleotide (−) for insertion into pGEXKT (OL16(−)).

SEQ ID NO: 14: oligonucleotide (+) for insertion into pET32a (OL18(+)) (hybridizes to the segment 915-932 of pGEXKT).

SEQ ID NOS: 15 and 16: respectively, oligonucleotides (+) (OL19(+)) and (−) (OL20(−)) for insertion into pT7-7 of the DNA encoding MDP-TME1.

SEQ ID NOS: 17 and 18: respectively, oligonucleotide (+) for insertion into pT7-7 (OL23(+)) and oligonucleotide (−) for insertion into pT7-7 (OL24(−)).

SEQ ID NOS: 19 and 20: respectively, coding sense DNA for TME2+Nde I site in the 5' position and Hind III site in the 3' position; and anticoding sense DNA of TME2+ Nde I site in the 3' position and Hind III site in the 5' position (sequence complementary to ID No. 17).

SEQ ID NOS: 21 and 22: respectively, coding sense oligonucleotide (OL21(+)) and anticoding sense oligonucleotide (OL22(−)) for the synthesis of THE2.

SEQ ID NO: 23: oligonucleotide (+) for insertion into pGEXKT without dp site (OL25(+)).

SEQ ID NOS: 24 and 25: respectively, oligonucleotides (+) (OL27(+)) and (−) (OL26(−)) for insertion into pGEXKT with dp site.

SEQ ID NOS: 26 and 27: respectively, oligonucleotides (+) (OL28(+)) and (−) (OL29(−)) for insertion into pT7-7 of the DNA encoding MDP-TME2.

SEQ ID NO: 28: end of the sequence of the GST soluble protein followed by the thrombin site encoded in the pGEXKT plasmid.

SEQ ID NO: 29: DNA encoding the GST protein in the pGEXKT plasmid.

SEQ ID NO: 30: DNA encoding thioredoxin (TrX) in the pFT32a+ plasmid.

SEQ ID NOS: 31, 32 and 33: respectively, pGEXKT, pET32a+ and pT7-7 expression plasmids.

SEQ ID NOS: 34, 35 and 36: respectively, expression systems according to the invention encoding the GST-DP-TME1, TrX-DP-TME1 and M-DP-TME1 fusion proteins.

SEQ ID NOS: 37, 38 and 39: respectively, expression systems according to the invention encoding the GST-DP-TME2, TrX-DP-TME2 and M-DP-TME2 fusion proteins.

SEQ ID NOS: 40 and 41: respectively, pGEXKT-dp-pt$_{TME1}$ and pGEXKT-dp-pt$_{TME2}$ expression vectors according to the invention encoding the GST-DP-TME1 and GST-DP-TME2 fusion proteins.

Sequences ID No. 42 and 43: respectively, pET32a-dp-pt$_{TME1}$ and pET32a-dp-pt$_{TME2}$ expression vectors according to the invention encoding the TrX-DP-TME1 and TrX-DP-TME2 fusion proteins (code via the complementary strand).

SEQ ID NOS: 44 and 45: respectively, pT7-7-dp-pt$_{TME1}$ and pT7-7-dp-pt$_{TME2}$ expression vectors according to the invention encoding the MDP-TME1 and M-DP-TME2 fusion proteins.

SEQ ID NOS: 46 and 47: respectively, GST-DP-TME1 and GST-DP-TME2 fusion proteins according to the invention obtained from the pGEXKT-dp-pt$_{TME1}$ and pGEXKT-dp-pt$_{TME2}$ plasmids.

SEQ ID NOS: 48 and 49: respectively, TrX-DP-TME1 and TrX-DP-TME2 fusion proteins according to the invention obtained from the pET32a-dp-pt$_{TME1}$ and pET32a-dp-pt$_{TME2}$ plasmids.

SEQ ID NOS: 50 and 51: respectively, M-DP-TME1 and M-DP-TME2 fusion proteins according to the invention obtained from the pT7-7-dp-pt$_{TME1}$ and pT7-7-dp-pt$_{TME2}$ plasmids.

SEQ ID NOS: 52 and 53: respectively, GST and TrX proteins encoded by the pGEXKT and pET32a+ vector.

EXAMPLES

Figure 1:
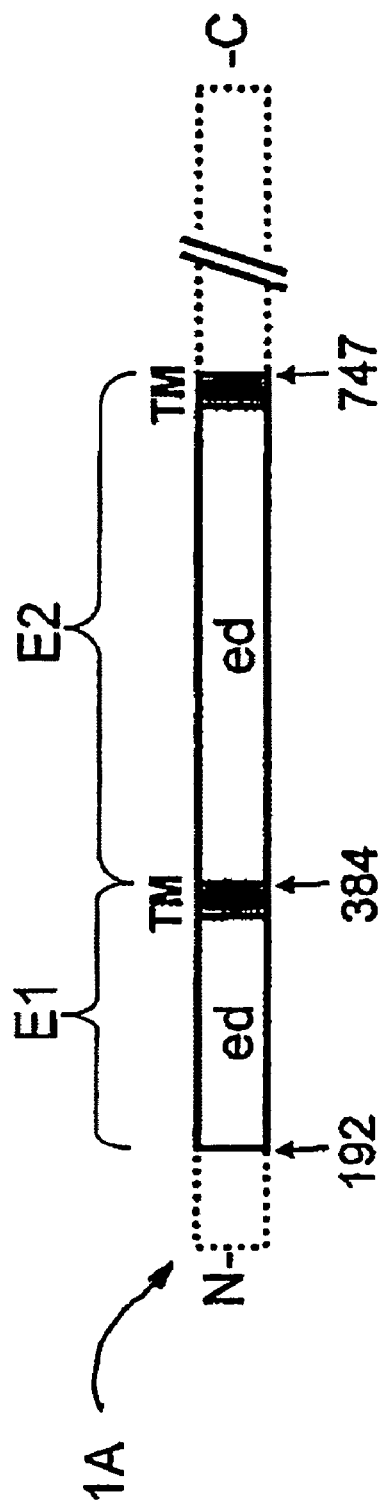
FIG. 1: diagrammatic representation of a portion of the HCV polyprotein and peptide sequence of the C-terminal membrane domains of the E1 and E2 envelope proteins. The peptide sequences represented correspond to the infectious type #D00831 and #M67463 for TME1 (SEQ ID NO: 1) and TME2 (amino acids 2-31 of SEQ ID NO: 2), respectively, obtained from the public sequence library of the European Molecular Biology This figure represents, at the top, the peptide sequences of GST (SEQ ID NO: 52) and GST-TME2, and, at the bottom, the gels obtained by electrophoresis, showing that, unlike GST alone, GST-TME2 is insoluble. The latter is produced in the form of inclusion bodies that cannot fold correctly.

In these examples, the oligonucleotides used were ordered from Laboratoires EUROBIO; the plasmids were prepared with the QIAprep kit (brand name) from Qiagen; the DNA sequences were sequenced with the ABI PRISM (registered trade mark) BigDye (brand name) Terminator cycle kit from Applied Biosystems; the E. coli strains BL21(DE3) and BL21 (DE3)pLysS were obtained from Stratagene; the C41 and C43 (BL21(DEF3)) strains were provided by Dr. Bruno Miroux (CNRS-CEREMOD, Centre for Research on molecular endocrinology and development; the DNA restriction and modification enzymes were obtained from New England Biolabs; the protein electrophoreses were carried out with a miniprotean 3 (brand name) from Bio Rad Laboratories; the plasmid pCR (registered trade mark) T7 topo TA was obtained from Invitrogen; the pET32a+ plasmid was obtained from Novagen; the pT7-7 and pGP1-2 plasmids and the K38 strain [22] were requested from Prof. Tabor (Department of Biological Chemistry, Harvard Medical School); the pGEX-KT plasmid was requested from Prof. Dixon (Department of Biological Chemistry, University of Michigan Medical School); the other products were obtained from Sigma.

In the following examples, the production of the TME1 and TME2 peptides was firstly carried out without the expression system of the present invention, and then as a fusion with a soluble protein and, finally, as a fusion with GST with insertion of the Asp-Pro ("DP" in one-letter coding) site between the soluble protein and TME1 or TME2.

The abbreviation "SEQ ID NO:" refers to the attached sequence listing.

Example 1

Synthesis of the Expression System 1.1) Construction of the pT7-7-pt$_{TME1}$ and pT7-7-pt$_{TME2}$ Expression Vectors The DNA encoding the two domains was synthesized de novo using the appropriate oligonucleotides. The codons were chosen according to their greatest frequency of use in the bacterium, as was quantified by Sharp et al. [17]. The constructs are described in the attached FIG. 2 for TME1 and in the attached FIG. 3 for TME 2.

Each synthetic DNA was generated using a set of two long and overlapping oligonucleotides, OL11 (SEQ ID NO: 9) and OL12 (SEQ ID NO: 10) for TME1, and OL21 (SEQ ID NO: 19) and OL22 (SEQ ID NO: 20) for TME2, which were amplified after hybridization with two external oligonucleotides chosen according to the cloning in a given plasmid. Thus, the clonings in pT7-7 were carried out using the set of external oligonucleotides OL13 (SEQ ID NO: 5) and OL14 (SEQ ID NO: 6) for TME1, and OL23 (SEQ ID NO: 15) and OL24 (SEQ ID NO: 16) for TME2.

Each synthetic DNA was generated using a set of four oligonucleotides: two long and overlapping and two short and external. The DNAs were amplified by the polymerase chain reaction method, referred to as "PCR"[18], and then cloned into a bacterial plasmid pCR (brand name) T7 topo TA. The synthesized DNAs were sequenced and then subcloned into the pT7-7 bacterial expression vector [19] using the Nde I restriction site in the 5' position and the Cla I or Hind III restriction site in the 3' position.

In FIG. 2:

A: TME1 peptide sequence of subtype #D00831. The numbering corresponds to the position of the sequence in the polyprotein as described in FIG. 1.

B: DNA sequence encoding the membrane domain with optimized codons for expression in the bacterium.

C and D: Strategy for DNA amplification without matrix. The coding sense and the anticoding sense of the oligonucleotides are indicated, respectively, by the signs (+) and (−). The long oligonucleotides overlap by about twenty bases so as to create the primer and then the matrix. The short oligonucleotides make it possible to amplify the matrix by PCR, integrating the desired restriction sites according to the plasmids used. The insertion into pT7-7 was carried out with the pair of oligonucleotides OL13 (SEQ ID NO: 5) and OL14 (SEQ ID NO: 6), via a subcloning in pCRT7 topo, integrating the Nde I and Hind III sites. The insertion into pGEXKT was carried out according to the same method, with the pair of oligonucleotides OL15 (SEQ ID NO: 11) and OL16 (SEQ ID NO: 13), integrating the BamH I and EcoR I sites. The insertion of the dp site (gacccg) and the cloning in pGEXKT were carried out with the pair of oligonucleotides OL17(SEQ ID NO: 12) and OL16 (SEQ ID NO: 13). The construct in pGEXKT was transferred into pET32a, which encodes thioredoxin, with the pair of oligonucleotides OL18 (SEQ ID NO: 14) and OL16 (SEQ ID NO: 13). The oligonucleotide OL18 (SEQ ID NO: 14) hybridizes in the terminal region of the DNA encoding GST in pGEXKT. The amplified sequence integrates the end of GST (SDLSGGGGG) followed by the thrombin site (LVPRGS) (SEQ ID NO: 28), by the DP site and by the membrane passage. After cloning, the DNA inserted into pET32a makes it possible to express the thioredoxin-SDLSGGGGGLVPRGS-DP-TME1 chimera (SEQ ID NO: 48).

In FIG. 3:

The legend is identical to FIG. 2, but the peptide sequence is that of subtype #M67463. The insertion into pT7-7 was carried out with the pair of oligonucleotides OL23 and OL24 (SEQ ID NO: 17 and SEQ ID NO: 18, respectively), via a subcloning in pCRT7 topo, integrating the Nde I and Hind III sites.

The insertion into pGEXKT was carried out according to the same method, with the pair of oligonucleotides OL25 and OL26 (SEQ ID NO: 23 and SEQ ID NO: 25, respectively), integrating the BamH I and EcoR I sites. Insertion of the dp site (gacccg) and the cloning in pGEXKT were carried out with the pair of oligonucleotides OL27 and OL26 (SEQ ID NO: 24 and SEQ ID NO: 25, respectively). Insertion into pET32a was carried out as described in FIG. 2, using the pair of oligonucleotides OL18 and OL26 (SEQ ID NO: 14 and SEQ ID NO: 25, respectively).

1.2) Construction of the pGEXKT-pt$_{TME1}$, pGEXKT-pt$_{TME2}$, pGEXKT-dp-pt$_{TME1}$ and pGEXKT-dp-pt$_{TME2}$ Expression Vectors The pGEXKT-pt$_{TME1}$ and pGEXKT-pt$_{TME2}$ expression vectors were constructed by PCR as described in the attached FIGS. 2 and 3. The matrix DNA used to amplify the DNAs encoding TME1 or TME2 is that cloned into the pT7-7 plasmids. The cloning of TME1 into the pGEXKT plasmid [20, 21] was carried out using the sets of oligonucleotides OL15 (SEQ ID NO: 11) and OL16 (SEQ ID NO: 13) allowing insertion of the BamH I restriction site in the 5' position and the EcoR I restriction site in the 3' position. The cloning of TME2 into the same vector was carried out using the sets of oligonucleotides OL25 (SEQ ID NO: 21) and OL26 (SEQ ID NO: 23).

As indicated in FIG. 2, the insertion of the dp site at the N-terminal position of TME1 was carried out by replacing the 5' oligonucleotide OL15 (SEQ ID NO: 11) with the oligonucleotide OL17 (SEQ ID NO: 12). The insertion of the dp site at the N-terminal position of TME2 was carried out by replacing the 5' oligonucleotide OL25 (SEQ ID NO: 21) with the oligonucleotide OL27 (SEQ ID NO: 22), as shown in FIG. 3.

1.3) Construction of the pET32a-dp-TME1 and pET32a-dp-TME2 Expression Vectors

The pET32a-dp-TME1 and pET32a-dp-TME2 expression vectors were constructed by PCR as described in the attached FIGS. 2 and 3, using the set of oligonucleotides indicated. The upstream oligonucleotide integrates an EcoR V site and hybridizes with the terminal region of the gene encoding GST. It makes it possible to integrate the 5-glycine tail and the thrombin-cleavage site present in the plasmid. The downstream oligonucleotide is the same as that used for the cloning in pGEXKT.

The insertion into the pET32a plasmid is carried out via the MsC I/EcoR V sites in the 5' position and the EcoR I site in the 3' position. It makes it possible to insert, in phase at the end of the thioredoxin sequence, the 5-glycine tail, the thrombin-cleavage site, the DP site and the membrane passage. The pET32a plasmid of origin, which serves as a control, encodes thioredoxin followed by a sequence integrating various elements that have not been deleted and that contribute, to a large degree, to the mass of the chimeric protein produced.

The matrix DNA used to amplify the DNAs encoding TME1 or TME2 is that cloned into the pGEXKT-dp-pt$_{TME1}$ or pGEXKT-dp-pt$_{TME2}$ plasmids. For TME, the cloning into pET32a+ was carried out using the sets of oligonucleotides OL18 (SEQ ID NO: 14) and OL16 (SEQ ID NO: 13). The cloning of TME2 into the same vector was carried out using the sets of oligonucleotides OL18 (SEQ ID NO: 14) and OL26 (SEQ ID NO: 23), as indicated in FIG. 3.

Example 2

Expression of Sequences Encoding the TME1 and TME2 Proteins Alone

The expression of the sequences encoding the TME1 and TME2 domains alone was tested by thermal or chemical induction and using various bacterial strains as described below.

2.1) Thermal Induction System

The system developed by Tabor [22] makes it possible to express a protein by thermal induction using two vectors in the same bacterium, pT7-7 and pGP1-2.

The pT7-7 plasmid contains the DNA to be expressed, placed under the control of a φ010 promoter recognized by the T7 phage RNA polymerase. The pGP1-2 plasmid contains the gene encoding the T7 phage polymerase, placed under the control of a $\lambda p_L$ promoter. This promoter is repressed by a thermosensitive repressor, cI857, that is itself also present in pGP1-2. At 30° C., cI857 is normally expressed and represses the $\lambda p_L$ promoter, which blocks the expression of the polymerase and therefore also that of the protein of interest.

The induction is triggered by switching the culture from 37 to 42° C. for 15-30 min, and then the expression continues at 37° C. This system is therefore particularly suitable when it is necessary to strictly control the expression of a given protein, in particular if said protein is toxic for the bacterium.

2.2 Chemical Induction System

The same pT7-7 plasmid containing the DNA to be expressed is this time introduced into *E. coli* bacteria of the type BL21(DE3) (B F$^-$ dcm omtP hsdS($r_B^- m_B^-$) gal λ (DE3)) and BL21(DE3)pLysS (B F$^-$ dcm ompT hsdS($r_B^- m_B^-$) gal λ (DE3) [pLysS Cam$^r$]). These bacteria have been modified so as to contain in the genome a copy of the gene encoding the T7 phage RNA polymerase, placed under the control of a lacUV5 promoter that can be induced with isopropyl-1-thio-β-D-galactoside (IPTG). In this case, the bacteria are cultured at their optimum temperature of 37° C. or less if necessary. The expression is induced by adding IPTG to the culture. The BL21(DE3)pLysS strain is particularly suitable for proteins whose base line expression is toxic for the host bacterium. In fact, the presence of the pLysS plasmid allows continuous expression, at a low level, of T7 phage lysozyme. This inhibits the T7 phage polymerase, the weak expression of which in the absence of induction could allow the base line expression of toxic protein.

The inventors also tested the expression of the membrane domains alone in strains called C41 and C43 [10], which were selected so as to withstand the expression of toxic membrane proteins. These strains are derived from the BL21(DE3) strain and are used in the same way as the latter.

2.3) Expression Tests

According to the system tested, the corresponding plasmids were introduced by transformation into the various strains of *E. coli*: K38 (HfrC λ) for the Tabor thermal induction system or the various BL21 strains for the chemical induction. Table 1 below summarizes the tests performed.

TABLE 1

| Induction | Strain | Plasmid |
|---|---|---|
| Thermal | K38 | pT7-7 + pGP1-2 |
| Chemical | BL21(DE3) | pT7-7 |
| Chemical | BL21(DE3)pLysS | pT7-7 |
| Chemical | C41(BL21(DE3)) | pT7-7 |
| Chemical | C43(BL21(DE3)) | pT7-7 |

In each case, about ten transformants were placed in culture in order to test the expression. Briefly, the bacteria were cultured in 5 ml of LB (10 g tryptone, 5 g yeast extract, 5 g NaCl, qs 1 liter H$_2$O), supplemented with 50 μg/ml of ampicillin (necessary in order to maintain pT7-7 in the bacterium) and 60 μg/ml of kanamycin (necessary in order to maintain pGP1-2 in the bacterium), and then cultured until saturation, either at 30° C. for K38 or at 37° C. for BL21(DE3). The cultures were then diluted to 1/10 in the same culture medium and cultured to an optical density (OD) of 1, measured at 600 nm on a Philips PU8740 spectrophotometer (brand name).

The expression was then induced either thermally (K38) at 42° C. for 15 min, or chemically (BL21(DE3)) by adding 1 mM IPTG. It was continued for 3-5 hours at 37° C. The $OD_{600\,nm}$ of the cultures was measured at various times.

At the end of the expression, a volume of culture containing the equivalent of 0.1 OD of bacteria was removed. The bacteria were harvested by centrifugation and suspended in 50 μl of lysis solution (LS: 50 mM Tris-Cl, pH 8.0, 2.5 mM EDTA, 2% SDS, 4 M urea, 0.7 M β-mercaptoethanol). After a few minutes at ambient temperature, 10 μl were loaded onto a 16.5% polyacrylamide gel for "Tricine" type electrophoresis [23], which makes it possible to obtain good separation of low molar mass proteins.

Figure 4:
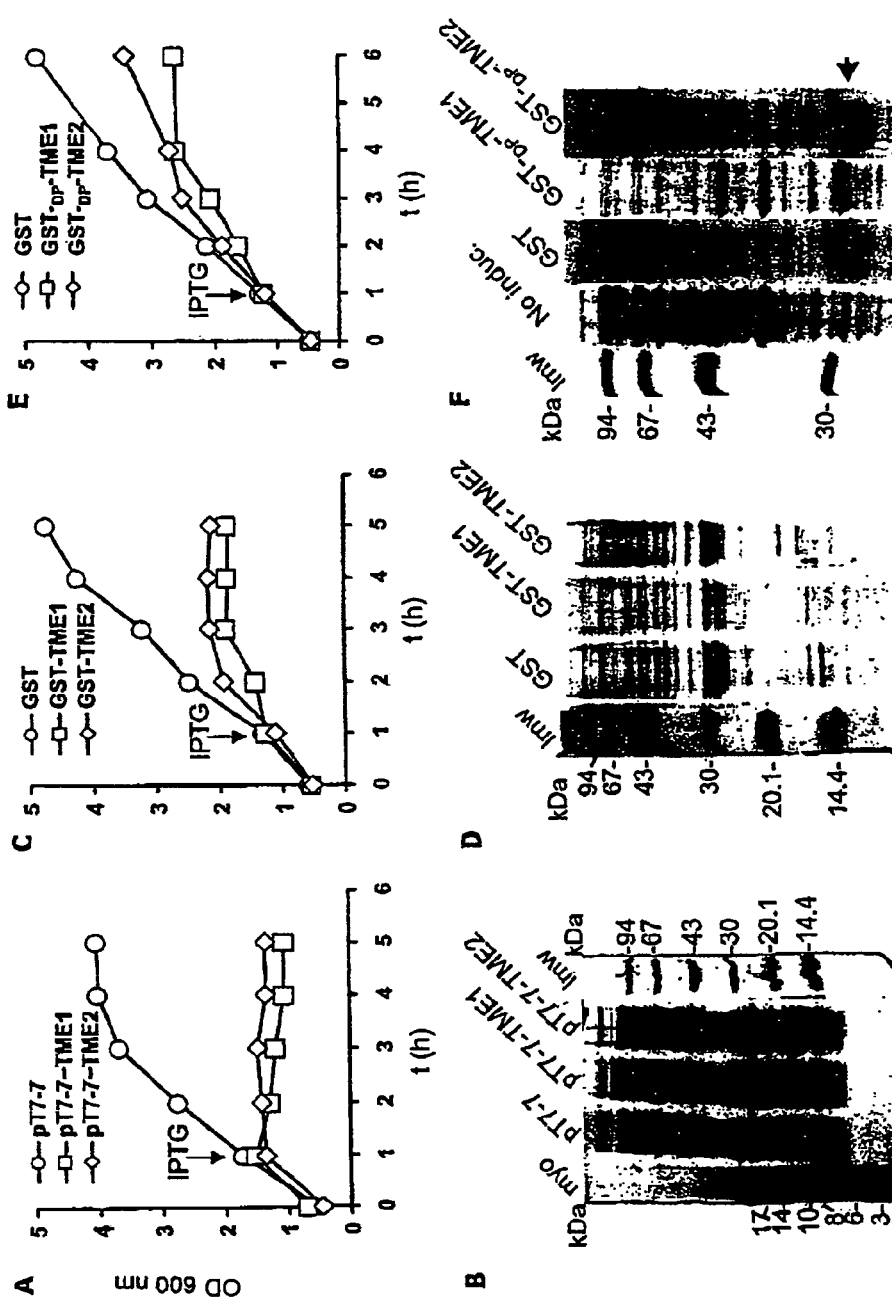

In FIG. 4:

Panels A, C and E: The bacteria were transformed with the plasmids pT7-7. pT7-7-TME1, pT7-7-TME2 (panel A), pGEXKT, pGEXKT-TME1, pGEXKT-TME2 (panel C), and pGEXKT-dp-TME1 and pGEXKT-dp-TME2 (panel E), and then cultured and induced as described above. The bacterial growth was followed by measuring the increase in turbidity of each culture by measuring the optical density at 600 nm as a function of the time in hours.

Panels B, D, F: The bacteria were sampled at the time indicated in the text and treated as described above. They were then deposited onto an electrophoresis gel, either 16.5% acrylamide of the "Tricine" type (panel B), or 14% acrylamide of the Laemmli SDS-PAGE type (panels D and F). The electrophoresis shown in panel F migrated for a longer period of time than that shown in panel D, in order to improve the separation of the bands in the 30 000 Da region. After migration, the gels were stained for 10 minutes with Coomassie blue in a solution of 40% methanol, 10% acetic acid and 0.1% Coomassie blue R250, and then destained in a solution of 10% methanol, 10% acetic acid and 1% glycerol.

Whatever the system tested, the first observation is that the frequency of transformation of the bacteria was low. For the bacteria that could be selected, the result of the expression tests was systematically negative. An example is given in FIG. 4, panels A and B, with the series BL21(DE3)pLysS {[pT7-7], [pT7-7 TME1] or [pT7-7-TME2]}. As illustrated by comparing the growth curves of panel A of FIG. 4, the inventors noted, with the clones transformed with pT7-7-TME1 or pT7-7-TME2 and resistant on solid medium, that the induction stops the bacterial growth virtually immediately, unlike the clones containing the plasmid alone. Similarly, as can be seen in FIG. 4(B), no band of proteins migrating in the region corresponding to the molecular mass of the expression products (~3-4000 Da) or of oligomers thereof ({1, 2, 3, etc.})× molecular mass) can in fact be observed.

The most probable explanation for this situation is that the expression of the membrane domains is very toxic for the bacterium. The difficulty in obtaining transformants implies that a base line expression, even very low, is sufficient to kill them. It also shows that the pLysS system is not perfect for preventing this base line expression. Among the bacteria that withstand the transformation step, the induction of expression of the hydrophobic domains becomes immediately lethal. The systems used effectively make it possible to protect the host bacterium against a base line expression, but as soon as this expression is induced, the toxicity is immediate and the bacteria are killed.

Example 3

Expression of Sequences Encoding the GST-TME1 and GST-TME2 Fusion Proteins

The expression vectors were constructed as described in Example 1, and then introduced into the BL21(DE3)pLysS bacteria. The BL21(DE3)pLysS bacteria were used in the interests of comparison with the preceding experiments since the expression of GST or of its chimeras does not require the DE3-pLysS system.

The expression was induced with IPTG as for that of the domains alone. The characteristics of the proteins produced are summarized in Table 2 below.

TABLE 2

| Plasmid | Chimera, abbreviation | Construct | Size, aa | Mass Da |
|---|---|---|---|---|
| pGEXKT | GST, G | $_1M\text{-}D_{239}$ | 239 | 27469 |
| pGEXKT-T1 | GST-TME1, GT1 | $_1M\text{-}S_{233\text{-}347}M\text{-}A_{383}$ | 269 | 30506 |
| pGEXKT-T2 | GST-TME2, GT2 | $_1M\_S_{233\text{-}717}E\text{-}A_{746}$ | 263 | 30191 |

The amino acids (aa) are indicated with the one-letter code. The numbering of the sequences is done with respect to the proteins of origin, GST and viral polyprotein. That which refers to the membrane domains is indicated in italics.

Panels C and D of the attached FIG. 4 show the results obtained. The growth curves for the bacteria transformed with the various plasmids show that expression of the GT1 and GT2 chimeras is toxic. As can be seen on the electrophoresis gel of the Laemmli SDS 14% PAGE type [24], the expression of TME1 fused to GST is accompanied by the absence of a band migrating at the expected size of 30 kDa. This implies that a very low level of expression of the chimera is sufficient to kill the bacteria. On the other hand, the GST-TME2 chimera is this time visible on the electrophoresis gel, in the region of expected molecular mass of 30 kDa. The level of expression remains limited however.

The protein produced is not soluble despite the presence of GST in the fusion. In fact, as shown in the attached FIG. 6, the solubilization, folding and purification trials for the GST-TME2 chimera were a failure.

To obtain the results represented in this FIG. 6, the GST and GST-TME2 proteins were expressed as described in FIG. 4, using 150 ml of culture medium. The bacteria were then harvested by centrifugation and suspended (20 mM $KPO_4$, pH 7.7, 0.1 M NaCl, 1 mM EDTA, 1 mM $NaN_3$) so as to have 1000D/ml. Two ml of each culture were removed for sonication with 30 sec pulses at an amplitude of 15%. After sonication, a sample is taken for electrophoresis. It corresponds to the well "To" in FIG. 6 (corresponding to the "total").

A first low-speed centrifugation (5000×g, 15 minutes) makes it possible to separate the non-ruptured bacteria and the inclusion bodies from the soluble or membrane proteins. The latter are found in the supernatant and a sample is taken. It corresponds to the well "Surn" in FIG. 6.

The fraction containing GST alone is then treated with an affinity resin that makes it possible to bind and then elute specifically this protein (well "Af" of the GST gel in FIG. 6).

The fraction containing the non-soluble GST-TME2 protein is treated either with a mild detergent such as triton X100 (TX100), in the presence or absence of NaCl, or with a more solubilizing but more destructuring detergent such as sarkosyl, before again being diluted in TX100 and passed over affinity resin.

The results in FIG. 6 show that GST is present in the soluble fraction, unlike the GST-TME2 fusion, which indicates that the latter is insoluble. The supernatant containing the GST is passed over an agarose-GSH resin capable of binding GST. This GST is then eluted with an excess of GSH (well marked "Af" of the GST gel in FIG. 6).

The pellet containing the GST-TMF2 fusion is not solubilized in the presence of a mild detergent such as TX100 (with or without added NaCl, well "TX100+/−NaCl" of the GST-TME2 gel), but it can be solubilized with a more aggressive detergent such as sarkosyl. However, after dilution of the protein thus solubilized in TX100, a mild detergent which should favour its folding, the protein is not retained on the affinity resin, unlike GST, which suggests that the fusion protein cannot be folded.

These tests clearly indicate that the GST-TME2 protein is produced in the form of inclusion bodies that cannot be correctly folded.

Example 4

Expression of Expression Vectors Encoding the Fusion Proteins Including an Asp-Pro site and a GST Site The construction of the vectors was carried out as described above and for the two vectors encoding the GST-TME1 and GST-TME2 chimeric proteins, so as to produce the vectors encoding the GST-Asp-Pro-TME1 and GST-Asp-Pro-TME2 chimeric proteins. They are summarized in Table 3 below.

TABLE 3

| Plasmid | Chimera, abbreviation FIG. 4 | Construct | Size, aa | Mass, Da |
|---|---|---|---|---|
| pGEXKT-dp-T1 | GST-DP-TME1; $G_{DP}T1$ | $_1M-D_{233}$-dp-$_{347}M-A_{383}$ | 271 | 30718 |
| pGEXKT-dp-T2 | GST-DP-TME2; $G_{DP}T2$ | $_1M-S_{233}$-dp-$_{717}E-A_{746}$ | 265 | 30403 |

The amino acids (aa) are indicated with the one-letter code. The numbering of the sequences is done with respect to the proteins of origin, GST and viral polyprotein. That which refers to the membrane domains is indicated in italics.

The vectors were tested as described in the preceding paragraph. The results obtained are shown on panels E and F of the attached FIG. 4.

The growth curves for the bacteria transformed with the various plasmids show that the expression of the $G_{dp}T1$ and $G_{dp}T2$ chimeras is clearly less toxic than in the previous cases. Panel F shows that, this time, TME1 is produced due to the presence of the DP cleavage site. Its level of expression, as can be seen in panel F, is relatively moderate, but significant. GST-DP-TME2 is clearly overproduced. The two proteins migrate in their expected molecular mass region.

The effect of the addition of the DP dipeptide is as significant as it is unexpected: it amplifies the expression of the domains and suppresses their toxicity. This effect of attenuation of the toxicity is not known for the DP dipeptide, the only property of which that has been reported to date is its ability to be cleaved by formic acid. Since the effect is observed on two different peptides that are both initially toxic for the bacterium, it is therefore reasonable to think that this property may extend to other hydrophobic and toxic peptides.

The inventors verified that the site can be effectively cleaved by formic acid: the cleavage is slow and requires approximately 7 days at ambient temperature.

The assays of expression at low temperature (20° C.) overnight of these chimeras made it possible to demonstrate that they are produced in native form. In fact, it is possible to detect CST transferase activity in the membrane fraction of the bacteria. In addition, this activity is measured in solution when the membranes are solubilized in the presence of a non-ionic detergent such as β-D-dodecylmaltoside, after centrifugation.

Example 5

Expression of Expression Vectors Encoding the Fusion Proteins Including an Asp-Pro Site and a Site Encoding Thioredoxin (TrX)

The pET32a-TrX, pET32a-TrX-dp-TME1 and pET32a-TrX-dp-TME2 expression vectors were constructed as described above and were then introduced into BL21(DE3) pLysS bacteria. The BL21(DE3)pLysS bacteria were used in the interests of comparison with the previous experiments since the expression of GST or of its chimeras does not require the DE3-pLysS system. The positive clones were cultured and induced as described above.

The induction of expression was carried out with IPTG, as for that of the domains alone. The characteristics of the proteins produced are summarized in Table 4 below.

TABLE 4*

| Plasmid | Chimera, abbreviation FIG. 4 | Construct | Size, aa | Mass, Da |
|---|---|---|---|---|
| pET32a | Thioredoxin; TrX | $_1M-C_{189}$ | 189 | 20397 |
| pET32a-Gend-dp-T1 | TrX-DP-TME1; $T_{DP}T1$ | $_1M-S_{115}$-PK-Gend-dp-$T_1$ | 171 | 17796 |
| pET32a-Gend-dp-T2 | TrX-DP-TME2; $T_{DP}T2$ | $_1M-S_{115}$-PK-Gend-dp-$T_2$ | 165 | 17481 |

*T1 = TME1 and T2 = TME2

The amino acids (aa) are indicated with the one-letter code. The numbering of the sequences is done with respect to the proteins of origin, GST and viral polyprotein. That which refers to the membrane domains is indicated in italics. "Gend" refers to the C-terminal sequence of the GST originating from the constructs with the pGEXKT plasmid. It corresponds to the primary peptide sequence SDLSGGGGGLVPRGS. The thioredoxin SDLSGGGGGLVPRGS-DP-(TME1 or TME2) chimeras are shorter than the protein encoded in the vector of origin since the insertion is effected immediately after the thioredoxin.

Figure 5:
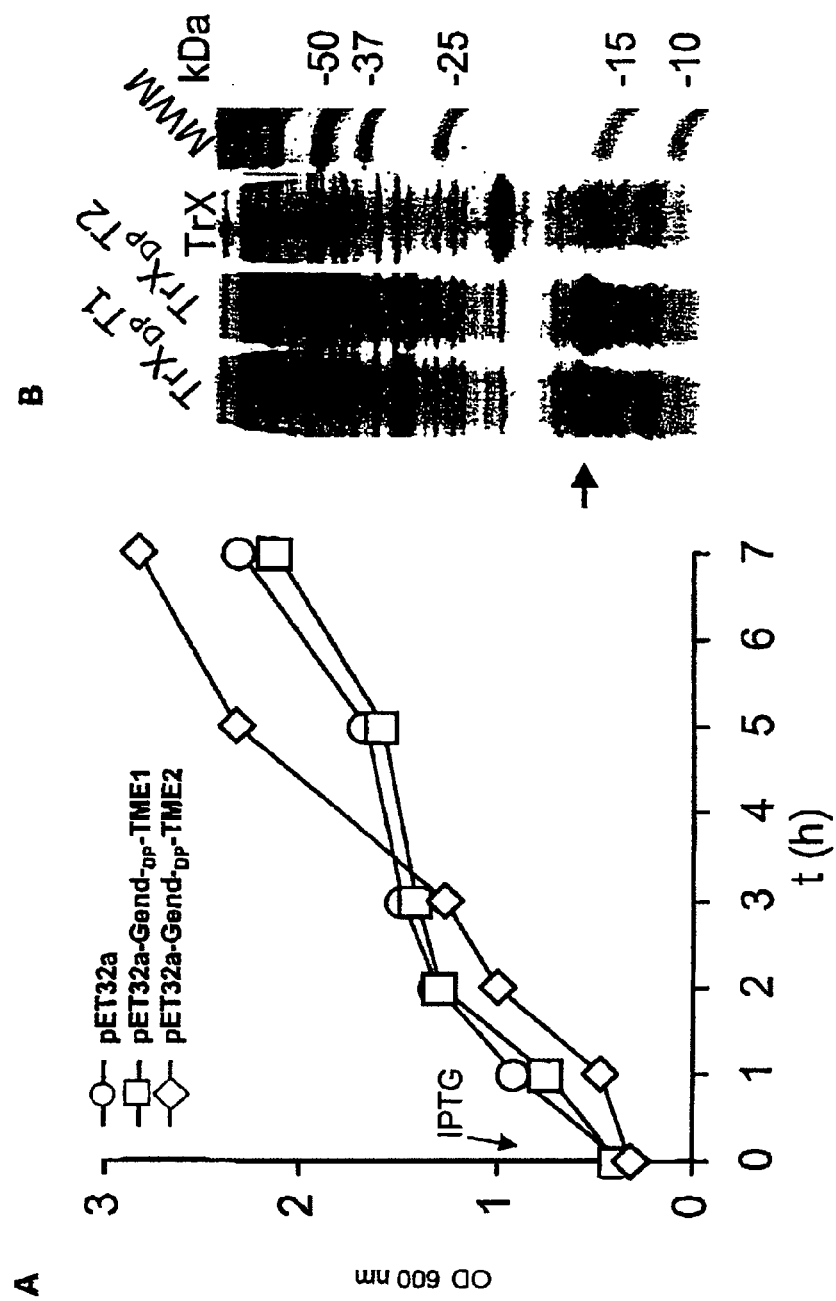

In FIG. 5:

A: the bacterial growth was followed by measuring the increase in turbidity of each culture by optical density at 600 nm as a function of time.

B: the bacteria were sampled as indicated for FIG. 4. They were then loaded onto a Laemmli SDS-PAGE type 14% acrylamide electrophoresis gel and treated as indicated for FIG. 4.

As expected, and as shown by the growth curves represented in the attached FIG. 5A for the bacteria transformed with the various plasmids, expression of the TrX-DP-TME1 and TrX-DP-TME2 chimeras according to the present invention is not toxic. The Laemmli 14% SDS-PAGE [24] electrophoresis gel represented in the attached FIG. 5B shows that each chimera is overproduced.

The present invention therefore makes it possible to produce, by genetic recombination, hydrophobic peptides corresponding to the membrane domains of the E1 and E2 proteins of the hepatitis C virus envelope, the expression of which was acknowledged to be lethal in the techniques of the prior art. In addition, since the effect is observed on two peptides that are really different and both initially toxic for the bacterium, this indicates that the present invention concerns other hydrophobic and toxic peptides.

Example 6

Effect of the DP Dipeptide on the Toxicity of the TME1 and TME2 Transmembrane Domains Expressed Without Fusion Protein in the Bacterium This example makes it possible to evaluate the antitoxic effect of the DP dipeptide inserted in the absence of CST or TrX fusion protein in accordance with the attached claim 1.

A) Materials: The pT7-7-pt$_{TME1}$ and pT7-7-pt$_{TME2}$ plasmids are those which are described in Example 1. The pT7-7-dp-pt$_{TME2}$ and pT7-7-dp-pt$_{TME2}$ plasmids were constructed and cloned in pT7-7 (SEQ ID NO: 33) as described in Example 1, but using the Nde I (5') EcoR I (3') sites of the plasmid. The upstream (5') oligonucleotides integrate the dp sequence (gacccg) after the 1st methionine (atg). The matrices used to generate each DNA were the pT7-7-pt$_{TME1}$ and pT7-7-pt$_{TME2}$ plasmids. The sequences were verified after cloning.

The oligonucleotides are as follows:

```
i) Cloning of the sequence encoding (M)DP-TME1 in
pT7-7:
OL19 (+):
5'-CGCATATGGACCCGATCGCTGGTGCT - 3' (Nde I under-
lined) =
(SEQ ID NO: 15 of the attached sequence listing);

OL20 (-):
5'-GAATTCCTAAGCGTCAACACCAGC-3' (EcoR I under-
lined) =
(SEQ ID NO: 16 of the attached sequence listing).

ii) Cloning of the sequence encoding (M)DP-TME2 in
pT7-7:
OL28 (+):
5'-CGCATATGGACCCGGAATACGTTGTTC-3' (Nde I under-
lined) =
(SEQ ID NO: 26 of the attached sequence listing);

OL29 (-):
5'-CAGAATTCCTAAGCTTCAGCCTGAGAG-3' (EcoR I under-
lined) =
SEQ ID NO: 27 of the attached sequence listing).
```

The pT7-7-dp-pt$_{TME1}$ and pT7-7-dp-pt$_{TME2}$ expression vectors obtained are given in the attached sequence listing (SEQ TD NO: 44 and SEQ ID NO: 45).

Figures 7A, 7B:
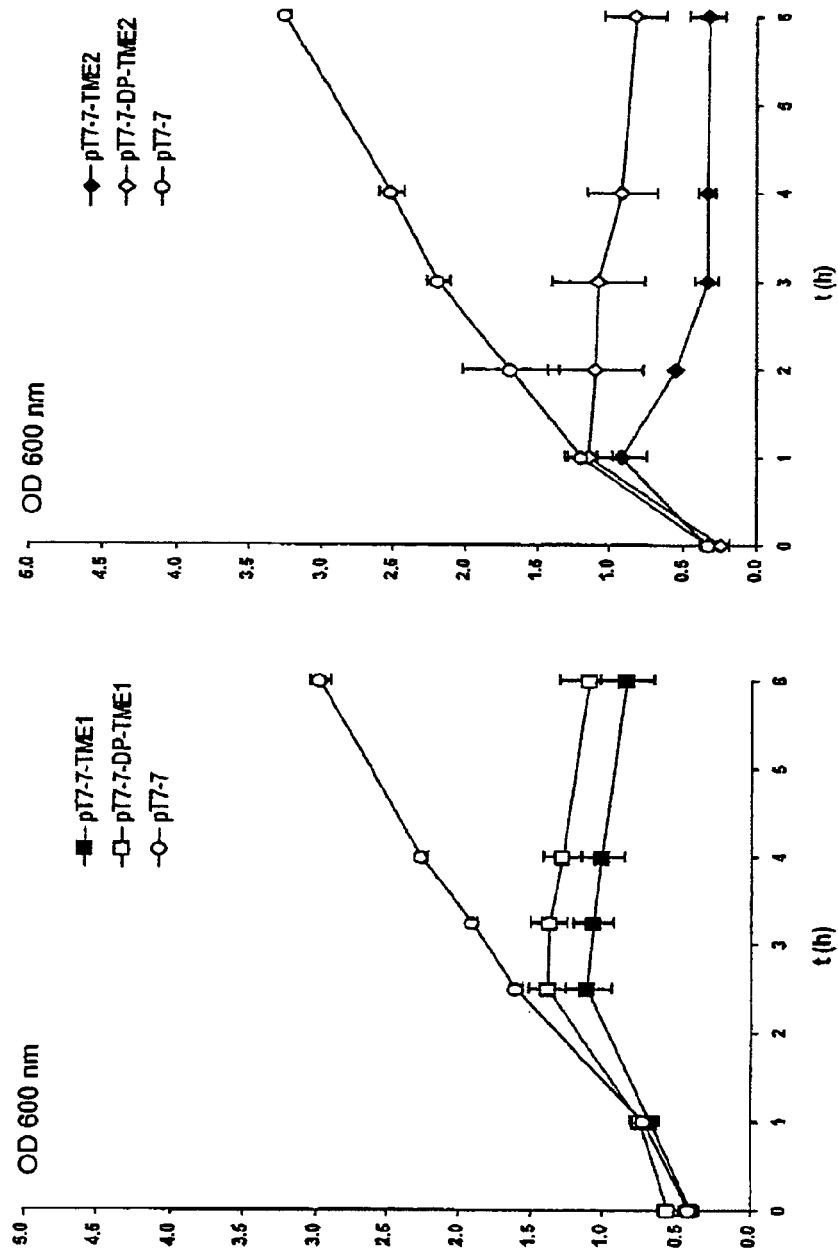
FIGS. 7A and 7B: graphic representations of comparative experimental results showing the effect of the DP dipeptide (dp-pt oligonucleotide sequence in accordance with the present invention) and of the DP dipeptide and the soluble protein (ps-dp-pt oligonucleotide sequence in accordance with the present invention) on the synthesis of the TME1 and TME2 toxic proteins in accordance with the present invention.

B) Legend of the attached FIGS. 7A and B: the bacterial strain BL21(DE3)pLysS was transformed either with the plasmid alone or with the various versions of pT7-7 integrating the 4 constructs expressing TME1, M-DP-TME1 (FIG. 7A), or TME2, M-DP-TME2 (FIG. 7B). M represents methionine; it is present at the N-terminal position of the peptides when the toxic proteins are produced according to the present invention with the pT7-7 plasmid.

The growth of the various clones was compared after induction with IPTG, according to the protocol identical to the chemical induction described in Example 2, and averaged over the OD values of 4 different clones for each construct.

C) Results:
FIGS. 7A and 7B show that the bacteria that have a plasmid expressing TME1 and TME2 proteins grow less rapidly after induction than the control strain which is transformed with the pT7-7 vector alone.

These results show that the strains transformed with the plasmids expressing the M-DP-TME1 (SEQ ID NO: 50) and M-DP-TME2 (SEQ ID NO: 51) versions according to the invention grow significantly better than those that express the TMs without DP. This is true for TME1, and even more clearly so for TME2.

The conclusion is that the N-terminal insertion of DP in accordance with the present invention contributes, surprisingly, to a significant decrease in toxicity of the expression of the membrane domains, in particular in the absence of a soluble fusion protein such as GST or thioredoxin.

REFERENCE LIST

[1] Christendat D., Yee A., Dharamsi A., Kluger Y., Gerstein M., Arrowsmith C. H., and Edwards A. M., (2000), *Prog. Biophys. Mol. Biol.* 73, 339-345;
[2] Hammarstrom M., Hellgren N., Van Den Berg S., Berglund H., and Hard T., (2002), *Protein Sci.* 11, 313-321;
[3] Falson P. (1992), *Biotechniques* 13, 20-22
[4] Falson P., Penin F., Divita G., Lavergne J. P., Di Pietro A., Goody R. S., and Gautheron D. C. (1993), *Biochemistry* 32, 10387-10397;
[5] Ciccaglione A. R., Marcantonio C., Costantino A., Equestre M., Geraci A. and Rapicetta M. (2000) *Virus Genes* 21, 223-226;
[6] Sisk W. P., Bradley J. D., Kingsley D., and Patterson T. A. (1992) *Gene* 112, 157-162;
[7] Paulsen I. T., Sliwinski M. K., Nelissen B., Goffeau A., and Saler M. H. Jr. (1998) *FEBS Lett* 430, 116-125;
[8] Decottignies A. and Goffeau A. (1997) *Nat Genet:* 15, 137-143;

[9] Arechage I., Miroux B., Karrasch S., Huijbregts R., de Kruijff B., Runswick M. J. and Walker J. E. (2000) *FEBS Lett* 482, 215-219;

[10] Miroux B., and Walker J. E. (1996) *J. Mol. Biol.* 260, 289-298;

[11] Mayo M. A., and Pringle C. R. (1998) *J. Gen Virol.* 79 (Pt4), 649-657;

[12] Op De Beeck A., Montserret R., Duvet S., Cocquerel L., Cacan R., Barberot B., Le Maire M., Penin F. and Dubuisson J. (2000) *J Biol Chem* 275, 31428-31437,

[13] Choo Q. L., Kuo G., Weiner A. J., Overby L. R., Bradley D. W., and Houghton M. (1989) *Science* 244, 359-362;

[14] Ciccaglione A. R., Marcantonio C., Costantino A., Equestre M., Geraci A. and Rapicetta M. (1996) *Virology* 250, 1-8;

[15] Ciccaglione A. R., Marcantonio C., Equestre M., Jones I. M. and Rapicetta M. (1998) *Virus Res* 55, 157-165,

[16] Op De Beeck A., Cocquerel L., and Dubuisson J. (2001) *J Gen Virol* 82, 2509-2595;

[17] Sharp P. M., Cowe E., Higgins D. G., Shields D. C., Wolfe K. H., and Wright F. (1990) *Nucleic Acids Res* 16, 8207-8211;

[18] Mullis K. S., and Faloona F. A. (1987) *Methods Enzymol* 135, 335-350;

[19] Tabor S. and Richardson C. C. (1985) *Proc Natl Acad Sci USA* 82, 1074-1078;

[20] Guan K. L., and Dixon J. E. (1991) *Anal Biochem* 192, 262-267;

[21] Hakes D. J., and Dixon J. E. (1992) *Anal Biochem* 202, 293-298;

[22] Tabor S. (1990) in *Current Protocols in Molecular Biology*, pp. 16.12.11-16.12.11, Greene Publishing and Wiley-Interscience, New York;

[23] Schagger H. and von Jagow G. (1987) *Anal Biochem* 166, 368-379;

[24] Laemmli U. K. (1970) *Nature* 227, 680-685.

[25] Sambrook, Fritsch and Maniatis, Molecular cloning, A laboratory manual, second edition, Cold spring Harbor Laboratory Press, 1989.

The invention claimed is:

1. An expression system comprising a DNA sequence, wherein said DNA sequence encodes a fusion protein comprising a sequence selected from the group consisting of SEQ ID NOS: 46-51.

2. An expression system comprising a DNA sequence encoding a fusion protein, wherein said DNA sequence is selected from the group consisting of SEQ ID NOS: 34-39.

3. A bacterial expression vector comprising:
(a) a DNA sequence, wherein said DNA sequence encodes a fusion protein comprising a sequence selected from the group consisting of SEQ ID NOS: 46-51, or
(b) a DNA sequence encoding a fusion protein, wherein said DNA sequence is selected from the group consisting of SEQ ID NOS: 34-39,
cloned into a plasmid.

4. A bacterial expression vector comprising a sequence selected from the group consisting of SEQ ID NOS: 40-45.

5. A prokaryotic cell transformed with the bacterial expression vector of claim 3.

6. The prokaryotic cell of claim 5, wherein the prokaryotic cell is an *E. coli* cell.

7. A method for producing a toxic membrane protein or a transmembrane domain of the toxic membrane protein by genetic recombination, comprising the following steps:
transforming a host cell with an expression vector,
culturing the transformed host cell under culture conditions such that it produces a fusion protein comprising the dipeptide Asp-Pro followed by the peptide sequence of the toxic membrane protein or the transmembrane domain of the toxic membrane protein from the expression vector, and
isolating the fusion protein;
wherein said expression vector
(a) comprises a DNA sequence, wherein said DNA sequence encodes a fusion protein comprising a sequence selected from the group consisting of SEQ ID NOS: 46-51;
(b) comprises a DNA sequence encoding a fusion protein, wherein said DNA sequence is selected from the group consisting of SEQ ID NOS: 34-39; or
(c) comprises a DNA sequence selected from the group consisting of SEQ ID NOS: 40-45.

8. The method of claim 7, wherein the method further comprises the following step:
cleaving the fusion protein so as to recover the toxic membrane protein or the transmembrane domain of the toxic membrane protein.

9. The method of claim 8, wherein the step of cleaving the fusion protein so as to recover the toxic membrane protein or the transmembrane domain of the toxic membrane protein is carried out by reacting the fusion protein with formic acid.

10. The method of claim 7, wherein the host cell is an *E. coli* cell.

11. The method of claim 7, wherein the expression vector comprises a DNA sequence, wherein said DNA sequence encodes a fusion protein comprising a sequence selected from the group consisting of SEQ ID NOS: 46-51.

12. The method of claim 7, wherein the expression vector comprises a DNA sequence encoding a fusion protein, wherein said DNA sequence is selected from the group consisting of SEQ ID NOS: 34-39.

13. The method of claim 7, wherein the expression vector comprises a DNA sequence selected from the group consisting of SEQ ID NOS: 40-45.

* * * * *